(12) United States Patent
Hoffman et al.

(10) Patent No.: US 8,058,227 B2
(45) Date of Patent: Nov. 15, 2011

(54) METHOD OF TREATING FIBROSIS IN A SUBJECT IN NEED THEREOF COMPRISING ADMINISTERING A COMPOSITION COMPRISING A CSD

(75) Inventors: Stanley Hoffman, Charleston, SC (US); Elena Tourkina, Charleston, SC (US)

(73) Assignee: Medical University of South Carolina, Charleston, SC (US)

( * ) Notice: Subject to any disclaimer, the term of this patent is extended or adjusted under 35 U.S.C. 154(b) by 157 days.

(21) Appl. No.: 11/866,994

(22) Filed: Oct. 3, 2007

(65) Prior Publication Data

US 2009/0075875 A1    Mar. 19, 2009

Related U.S. Application Data

(60) Provisional application No. 60/828,009, filed on Oct. 3, 2006.

(51) Int. Cl.
*A61K 38/00* (2006.01)
*A61K 38/10* (2006.01)
*A61P 17/02* (2006.01)

(52) U.S. Cl. ................ 514/1.1; 514/9.4; 514/21.4

(58) Field of Classification Search .............. None
See application file for complete search history.

(56) References Cited

U.S. PATENT DOCUMENTS 7,494,976 B2 * 2/2009 Sessa ................ 514/12

OTHER PUBLICATIONS

Tourkina et al., J.Biol. chem. 280:13879-13887, 2006.*
Wells, 1990, Biochemistry 29:8509-8517.*
Bowie et al., Science 247: 1306-1310, 1990.*
Anderson RG. The caveolae membrane system. Annu Rev Biochem , 67:199-225, 1998.
Bellini A, Mattoli S. The role of the fibrocytes, a bone marrow-derived mesenchymal progenitor, in reactive and reparative fibrosis. Lab Invest, 2007.
Beon M, Harley RA, Wessels A, Silver RM, Ludwicka-Bradley A. Myofibroblast induction and microvascular alteration in scleroderma lung fibrosis. Clin Exp Rheumatol, 22: 733-742, 2004.
Bernatchez P, Bauer P, Yu J, Prendergast J, He P, Sessa W. Dissecting the molecular control of endothelial NO synthase by caveolin-1 using cell-permeable peptides. Proc Natl Acad Sci U S A, 102:761-766, 2005.
Bogatkevich GS, Tourkina E, Silver RM, Ludwicka-Bradley A. Thrombin differentiates normal lung fibroblasts to a myofibroblast phenotype via the proteolytically activated receptor-1 and a protein kinase C-dependent pathway. J Biol Chem , 276:45184-45192, 2001.
Bogatkevich GS, Tourkina E, Abrams CS, Harlley CA, Silver RM, Ludwicka-Bradley A. Contractile Activity and Smooth Muscle alpha-actin organization in thrombin-induced human lung myofibroblasts. Am. J. Physiol Lung CEll Mol Physiol, 85:L334-L343, 2003.
Bucci M, Gratton J-P, Rudic RD, Acevedo L, Roviezzo F, Cirino G, Sessa WC. In vivo delivery of the caveolin-1 scaffolding domain inhibits nitric oxide synthesys and reduces inflammation. Nature Med, 6:1362-1367, 2000.
Cohen AW, Park DS, Woodman SE, Williams TM, Chandra M, Shirani J, Pereira de Souza A, Kitsis RN, Russell RG, Weiss LM. Caveolin-1 null mice develop cardiac hypertrophy with hyperactivation of p42/44 MAP kinase in cardiac fibroblasts. Am J Physiol Cell Physiol 284:C457-474, 2003.
Couet J, Sargiacomo M, and Lisanti, MP. Interaction of a receptor tyrosine kinase, EGF-R, with caveolins. Caveolin binding negatively regulates tyrosine and serine/threonine kinase activities. J Biol Chem 272:30429-30438, 1997.
Cui J, Holgado-Magruda M, Su W, Tsuiki H, Wedegaertner P, Wong AJ. Identification of specific domain responsible for JNK2alpha2 autophosphorylation. J. Biol. Chem. 280:9913-9920, 2005.
Drab M, Vercade P, Elger M, Kasper M, Lohn M, Lauterbach B., Menne J., Lindschau C., Mende F., Luft F. C., Schedl A., Haller H., and Kurzchalia T. V. Loss of caveolae, vascular dysfunction, and pulmonary defects in caveolin-1 gene-disrupted mice. Science, 293:2449-2452, 2001.
Finch WR, Rodnan GP, Buckingham RB, Prince RK, Winkelstein A. Bleomycin-induced scleroderma. J Rheumatol ,7:651-659, 1980.
Galbiati F, Volonte D, Gil O, Zanazzi G, Salzer J, Sargiacomo M, Scherer PE, Engelman JA, Schlegel A, Parenti M. Expression of caveolin-1 and -2 in differentiating PC12 cells and dorsal root ganglion neurons: caveolin-2 is up-regulated in response to cell injury. Proc Natl Acad Sci U S A, 95:10257-10262, 1998.
Gray AJ, Bishop JE, Reeves JT, Mecham RP, Laurent GJ. Partially degraded fibrin(ogen) stimulates fibroblast proliferation in vitro. Am J Respirator Cell Mol Biol, 12: 684-690, 1995.
Hong KM, Belperio JB, Keane MP, Burdick MD, Strieter RM. Differentiation of human circulating fibrocytes as mediated by transforming growth factor-beta and peroxisome proliferators activated receptor-gamma. J Biol Chem, 2007.
Hua H, Munk S, Whiteside CI. Endothelin-1 activates mesangial cell ERK1/2 via EGF-receptor transactivation and caveolin-1 interaction. Am J Physiol Renal Physiol, 284:F303-312, 2003.
Kasper M, Reimann T, Hempe, U, Wenze KW, Bierhaus A, Schuh D, Dimmer V, Haroske G, Muller M. Loss of caveolin-1 expression in type I pneumocytes as an indicator of subcellular alterations during lung fibrogenesis. Histochem Cell Biol, 109:41-48, 1998.
Kim KK, Kudler MC, Wolters PJ, Robillard L, Galvez MG, Brumwell AN, Sheppard D, Chapman NA. Alveolar epithelial cell mesenchymal transition develops in vivo during pulmonary fibrosis and is regulated by the extracellular matrix. Proc Natl Acad Sci USA, 103: 13180-13185, 2006.
Lisanti M, Scherer P, Vidugiriene J, Tang Z, Hermanowski-Vosatka A, Tu Y-H, Cook R, Sargiacomo M. Characterization of caveolin-rich membrane domains isolated from an endothelial-rich source: implications for human disease. J Biol Chem, 126: 111-126, 1994.
Mimura Y, Ihn H, Jinnin M, Asano Y, Yamane K, Tamaki K. Constitutive phosphorylation of focal adhesion kinase is involved in the myofibroblast differentiation of scleroderma fibroblasrs. J Invest Dermatol, 124: 886-892, 2005.
Moore BB, Kolodsick JE, Thanninckal VJ, Cooke K, Moore TA, Hogaboam C, Wilke CA, Toews GB. CCR2-mediated recruitment of fibrocytes to the alveolar space after fibrotic injury. Am J Pathol, 166: 675-684, 2005.
Oka N, Yamamoto M, Schwencke C, Kawabe J-I, Ebina T, Ohno S, Couet J, Lisanti MP, Ishikawa Y. Caveolin interaction with protein kinase C. J Biol Chem, 272:33416-33421, 1997.

(Continued)

*Primary Examiner* — Gyan Chandra
(74) *Attorney, Agent, or Firm* — Ballard Spahr LLP

(57) ABSTRACT

Disclosed are compositions and methods for the treatment of fibrosis. Also disclosed are methods of screening for agents that treat fibrosis.

10 Claims, 15 Drawing Sheets

OTHER PUBLICATIONS

Figure 1:
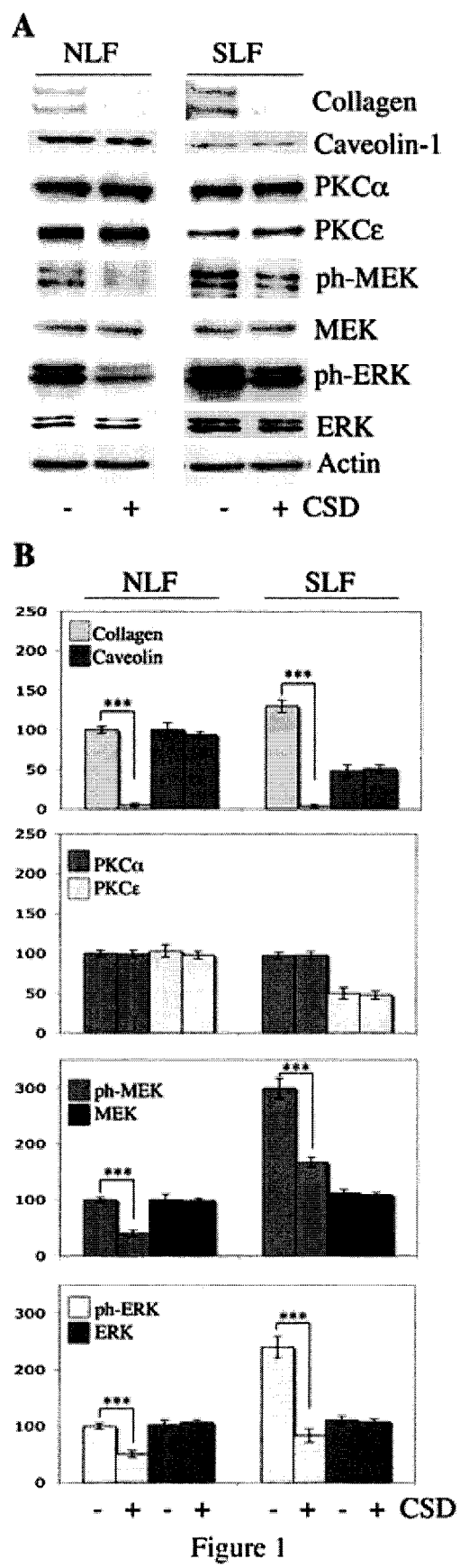

Okamoto T, Schlegel A, Scherer PE, Lisanti MP. Caveolins, a family of scaffolding proteins for organizing 'pre-assembled signaling complexes' at the plasma membrane. J Biol Chem, 273:5419-5422, 1998.

Pannu J, Nakerakanti S, Smith E, Dijke P, and Trojanowska M. Transforming Growth Factor-beta receptor type I-dependent fibrogenic gene programls mediated via activation of Smad1 and ERK1/2 pathways. J Biol Chem, 282; 10405-10413, 2007.

Phillips RJ, Burdick MD, Hong K, Lutz MA, Murray LA, Xue YY, Belperio JA, Keane MP, Strieter RM. Circulating fibrocytes traffic to the lungs in response to CXCL12 and mediate fibrosis. J Clin Invest, 114: 438-446, 2004.

Quan TE, Cowper SE, Bucala R. The role of the circulating fibrocytes in fibrosis. Curr Rheumatol Rep, 8: 145-150, 2006.

Razani B, Rubin CS, Lisanti MP. Regulation of cAMP-mediated signal transduction via interaction of caveolins with the catalitic subutit of protein kinase A. J Biol Chem, 274:26353-26360, 1999.

Razani B, Engelman JA, Wang XB, Schubert W, Zhang XL, Marks CB, Macaluso F, Russel, RG, Li M, Pestell RG, Di Vizio D, Hou H Jr, Kneitz B, Lagaud G, Christ GJ, Edelmann W, Lisanti MP. Caveolin-1 null mice are viable but show evidence of hyperproliferative and vascular abnormalities. J Biol Chem, 276:38121-38138, 2001.

Razani B, Woodman S, Lisanti M. Caveolae: from cell biology to animal physiology. Pharmacol Rev, 54:431-467, 2002.

Rybin VO, Xu X, Steinberg SF. Activated protein kinase C isoforms target to cardiomyocyte caviolae: stimulation of local protein phosphorylation. Circ Res, 84: 980-988, 1999.

Scherer PE, Tang Z., Chun M, Sargiacomo M, Lodish HF, Lisanti MP. Caveolin isoforms differ in their N-terminal protein sequence and subcellular distribution. Identification and epitope mapping of an isoform-specific monoclonal antibody probe. J Biol Chem , 270:16395-16401, 1995.

Sedding DG, Hermsen J, Seay U, Eickelberg O, Kummer W, Schwencke C, Strasser RH, Tillmanns H, and Braun-Dullaeus RC. Caveolin-1 facilitates mechanosensitive protein kinase B (Akt) signaling in vitro and in vivo. Circ Res 96; 635-642, 2005.

Shaul P and Anderson R. Role of plasmalemmal caveolae in signal transduction. AJP Lung Cell Mol Phys, 275:L843-L851, 1998.

Shi-wen X, Chen Y, Denton CP,Eastwood M, Renzoni EA, Bou-Gharios G, Pearson JD, Dashwood M, duBois RM, Black CM, Leask A, Abraham DJ. Endothelin-1 promotes myofibroblast induction through the ETA receptor via a rac/PI3 kinase/Akt-dependent pathway and is essential for the enhanced contractile phenotype of fibrotic fibroblasts. MBC,15: 2707-2719, 2004.

Shi-Wen X, Rodriguez-Pascual F, Lamas S, Holmes A, Howat S, Pearson JP, Dashwood MR, du Bois RM, Denton CP, Black CM, Abraham DJ, and Leask A. Constitutive ALK5-independent c-Jun N-Terminal Kinase activation contributes to endothelin-1 overexpression in pulmonary fibrosis: evidence of an autocrine endothelin loop operating through the endothelin A and B receptors. Mol Cel Biol, 26; 5518-5527, 2006.

Song KS, Li S, Okamoto T, Guilliam LA, Sargiacomo M, Lisanti MP. Co-precipitation and direct interaction of Ras with caveolin, an integral membrane protein of caveolae microdomains. J Biol Chem, 271:9690-9697, 1996.

Sowa G, Pypaert M, Sessa W. Distinction between signaling mechanisms in lipid rafts vs. caveolae. Proc Natl Acad Sci U S A, 98: 14072-14077, 2001.

Steen VD, Medsger TA. Changes in causes of death in systemic sclerosis. Ann Rheum Dis, 66: 940-944, 2007.

Tashkin DP, Elashoff R, Clements PJ, Goldin J, Roth MD, Furst DE, Arriola E, Silver J, Strange C. Bolster M, Seibold JR, Riley DJ, Hsu VM, Varge J, Schaufnagel DE, Theodore A, Simms R, Wise R, Wigley F, White B, Steen V, Read C, Mayes M, Parsley E, Mubarak K, Connoly MK, Golden J, Olman M, Fessler B, Rothfield N, Metersky M. Scleroderma Lung Study Research Group. Cyclophosphamide versus placebo in scleroderma lung disease. N Engl J Med, 354: 2655-2666, 2006.

Thannickal VJ, Lee DY, White ES, Cui Z, Larios JM, Chacon R, Horowitz JC, Day RM, Thomas PR. Myofibroblast differentiation by transforming growth factor-beta 1 is dependent on cell adhesion and integrin signaling via focal adhesion kinase. J Biol Chem, 278: 12384-12389, 2003.

Toker A, and Newton A. Akt/Protein Kinase B regulated by autophosphorylation in the hypothetical PDK-2 site. J Biol Chem, 275: 8271-8274, 2000.

Tourkina E, Hoffman S, Fenton JW II, Silver RM, Ludwicka-Bradley A. Depletion of PKC-epsilon in normal and scleroderma lung fibroblasts has opposite effects on tenascin expression. Arthritis and Rheum, 44:1370-1381, 2001.

Tourkina E, Gooz P, Oates JC, Ludwicka-Bradley A, Silver RM, Hoffman S. Curcumin-induced apoptosis in scleroderma lung fibroblasts: Role of protein kinase Ce. American Journal of Respiratory Cellular and Molecular Biology, 31:28-35, 2004.

Tourkina E, Gooz P, Pannu, J, Bonner M, Scholz D, Hacker S, Silver RM, Trojanowska M, and Hoffman S. Opposing effects of protein kinase C alpha and protein kinase C epsilon on collagen expression by human lung fibroblasts are mediated via MEK/ERK and caveolin-1 signaling. J Biol Chem , 280:13879-13887, 2005.

Tourkina E, Richard M, Charles K, Silver RM, Hoffman S. Caveolin-1 regulates collagen expression through MEK/ERK signaling and differentiation normal lung fibroblasts in myofibroblasts. ASCB Meeting, Washington, DC, Dec. 2005, Abstract.

Tourkina E, Richard M, Bonner M, Silver RM, Hoffman S. Antifibrotic and anti-inflammatory roles of caveolin-1 in scleroderma. ASCB Meeting, San-Diego, Dec. 2006, Abstract.

Uhal B, Joshi I, Hughes WF, Ramos C, Pardo A, Selman M. Alveolar epithelial cell death adjacent to underlying myofibroblasts in advanced fibrotic human lung. Am J Physiol Lung Cell Mol Physiol 1998; 275:L1192-L1199.

Van de Water J, Jiminez SA, Gershwin ME. Animal models of scleroderma: contrasts and comparisons. Intern Rev Immunol 1995; 12:201-216.

Vyalov Sl, Gabbiani G, and Kapanci Y. Rat alveolar myofibroblasts acquire alpha-smooth muscle actin expression during bleomycin-induced pulmonary fibrosis. Am J Pathol 1993; 143: 1754-1765.

Wang Xm, Zhang Y, Kim HP, Zhou Z, Feghali-Bostwick CA, Liu F, Ifedigbo E, Xu X, Oury TD, Kaminski N, and Choi AMK. Caveolin-1: a critical regulator of lung fibrosis in idiopathic pulmonary fibrosis. J Exp Med, 203; 2895-2906, 2006.

White ES, Atrasz RG, Hu B, Phan SH, Stambolic V, Mac TW, Hogaboam CM, Flaherty KR, Martinez FJ, Kontos CD, Toews GB. Negative regulation of myofibroblast differentiation by PTEN (Phosphatase and Tensin Homolog deleted on chromosome 10). Am J Respir Crit Care Med, 173: 112-121, 2006.

Wu Z, Yang L, Cai L, Zhang M, Cheng X, Yang X, Xu J. Detection of epithelial to mesenchymal transition in airways of a bleomycin induced pulmonary fibrosis model derived from an alpha-smooth muscle actin-Cre transgenic mouse. Respir Res, 8: 1, 2007.

Yamamoto T, Takagawa S, Katayama I, Yamazaki Y, Shinkai H, Nashioka K. Animal model of sclerotic skin I: local injections of bleomycin induce sclerotic skin mimicking scleroderma. J Invest Dermatol, 112:456-462, 1999.

Zhang H, Gharaee-Kermani M, Zhang K, Karmiol S, Phan SH. Lung fibrosis, alpha-smooth muscle actin expression and contractile phenotype in bleomycin-induced pulmonary fibrosis. Am J Pathol, 148:527-537, 1996.

Silver, R.M. 1995. Interstitial lung disease of systemic sclerosis. Int Rev Immunol 12:281-291.

Altman, R.D., Medsger, T.A., Jr., Bloch, D.A., and Michel, B.A. 1991. Predictors of survival in systemic sclerosis (scleroderma). Arthritis Rheum 34:403-413.

Couet, J., Li, S., Okamoto, T., Ikezu, T., and Lisanti, M.P. 1997. Identification of peptide and protein ligands for the caveolin-scaffolding domain. Implications for the interaction of caveolin with caveolae-associated proteins. J Biol Chem 272:6525-6533.

Muller, G., Jung, C., Wied, S., Welte, S., Jordan, H., and Frick, W. 2001. Redistribution of glycolipid raft domain components induces insulin-mimetic signaling in rat adipocytes. Mol Cell Biol 21:4553-4567.

Wender, P.A., Mitchell, D.J., Pattabiraman, K., Pelkey, E.T., Steinman, L., and Rothbard, J.B. 2000. The design, synthesis, and evaluation of molecules that enable or enhance cellular uptake: peptoid molecular transporters. Proc Natl Acad Sci U S A 97:13003-13008.

* cited by examiner

SEQUENCE LISTING

```
<160> NUMBER OF SEQ ID NOS: 19

<210> SEQ ID NO 1
<211> LENGTH: 20
<212> TYPE: PRT
<213> ORGANISM: Homo sapien

<400> SEQUENCE: 1

Asp Gly Ile Trp Lys Ala Ser Phe Thr Thr Phe Thr Val Thr Lys Tyr
1               5                   10                  15

Trp Phe Tyr Arg
            20

<210> SEQ ID NO 2
<211> LENGTH: 20
<212> TYPE: PRT
<213> ORGANISM: Artificial Sequence
<220> FEATURE:
<223> OTHER INFORMATION: synthetic construct

<400> SEQUENCE: 2

Trp Gly Ile Asp Lys Ala Phe Phe Thr Thr Ser Thr Val Thr Tyr Lys
1               5                   10                  15

Trp Phe Arg Tyr
            20

<210> SEQ ID NO 3
<211> LENGTH: 16
<212> TYPE: PRT
<213> ORGANISM: Drosophilia melanogaster

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 11
<212> TYPE: PRT
```

```
<213> ORGANISM: Artificial Sequence
<220> FEATURE:
<223> OTHER INFORMATION: synthetic construct

<400> SEQUENCE: 4

Trp Gly Phe Gly Lys Gln Gly Phe Gln Cys Gln
1               5                   10

<210> SEQ ID NO 5
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2
<223> OTHER INFORMATION: Xaa=Ser or Thr
<220> FEATURE:
<221> NAME/KEY: VARIANT
<222> LOCATION: 3
<223> OTHER INFORMATION: Xaa=Phe or Tyr
<220> FEATURE:
<221> NAME/KEY: VARIANT
<222> LOCATION: 4
<223> OTHER INFORMATION: Xaa=Val or Thr
<220> FEATURE:
<221> NAME/KEY: VARIANT
<222> LOCATION: 7
<223> OTHER INFORMATION: Xaa=Gln, Glu,Lys,or Asp
<220> FEATURE:
<221> NAME/KEY: VARIANT
<222> LOCATION: 9
<223> OTHER INFORMATION: Xaa=Val or Glu
<220> FEATURE:
<221> NAME/KEY: VARIANT
<222> LOCATION: (10)...(10)
<223> OTHER INFORMATION: Xaa=His or Ile
<220> FEATURE:
<221> NAME/KEY: VARIANT
<222> LOCATION: (11)...(11)
<223> OTHER INFORMATION: Xaa=Pro, Asn or Leu

<400> SEQUENCE: 5

Phe Xaa Xaa Xaa Asn Pro Xaa Phe Xaa Xaa Xaa
1               5                   10

<210> SEQ ID NO 6
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 5
<223> OTHER INFORMATION: Xaa=Pro or Ala
<220> FEATURE:
<221> NAME/KEY: VARIANT
<222> LOCATION: 6
<223> OTHER INFORMATION: Xaa=Asn or Ser
<220> FEATURE:
<221> NAME/KEY: VARIANT
<222> LOCATION: 9
<223> OTHER INFORMATION: Xaa=Lys, Ser or Arg
<220> FEATURE:
<221> NAME/KEY: VARIANT
<222> LOCATION: 10
<223> OTHER INFORMATION: Xaa =Glu or His

<400> SEQUENCE: 6

Phe Met Tyr Pro Xaa Xaa Pro Trp Xaa Xaa Ile
1               5                   10
```

```
<210> SEQ ID NO 7
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2
<223> OTHER INFORMATION: Xaa-Gly or Thr
<220> FEATURE:
<221> NAME/KEY: VARIANT
<222> LOCATION: 9
<223> OTHER INFORMATION: Xaa=Ala or Ser
<220> FEATURE:
<221> NAME/KEY: VARIANT
<222> LOCATION: 10
<223> OTHER INFORMATION: Xaa=Phe or Leu

<400> SEQUENCE: 7

Tyr Xaa Phe Ser Val Asp Trp Trp Xaa Xaa Gly
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: Xaa=His or Tyr
<220> FEATURE:
<221> NAME/KEY: VARIANT
<222> LOCATION: 2
<223> OTHER INFORMATION: Xaa=Ser or Asn
<220> FEATURE:
<221> NAME/KEY: VARIANT
<222> LOCATION: 5
<223> OTHER INFORMATION: Xaa=Ala or Ser
<220> FEATURE:
<221> NAME/KEY: VARIANT
<222> LOCATION: 10
<223> OTHER INFORMATION: Xaa=Asp or Glu
<220> FEATURE:
<221> NAME/KEY: VARIANT
<222> LOCATION: 11
<223> OTHER INFORMATION: Xaa=His or Tyr

<400> SEQUENCE: 8

Xaa Xaa Tyr Lys Xaa Pro Thr Phe Cys Xaa Xaa
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 3
<223> OTHER INFORMATION: Xaa=Tyr or Phe
<220> FEATURE:
<221> NAME/KEY: VARIANT
<222> LOCATION: 5
<223> OTHER INFORMATION: Xaa=Val or Thr
<220> FEATURE:
<221> NAME/KEY: VARIANT
<222> LOCATION: 6
<223> OTHER INFORMATION: Xaa=Asn or Gln
<220> FEATURE:
<221> NAME/KEY: VARIANT
<222> LOCATION: 8
<223> OTHER INFORMATION: Xaa=Phe or Tyr
```

```
<220> FEATURE:
<221> NAME/KEY: VARIANT
<222> LOCATION: 9
<223> OTHER INFORMATION: Xaa=Cys, Ala or Gly

<400> SEQUENCE: 9

His Pro Xaa Leu Xaa Xaa Leu Xaa Xaa Cys Phe
 1               5                   10

<210> SEQ ID NO 10
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: Xaa=Phe or Trp
<220> FEATURE:
<221> NAME/KEY: VARIANT
<222> LOCATION: 2
<223> OTHER INFORMATION: Xaa=Ala, Ser or Gly
<220> FEATURE:
<221> NAME/KEY: VARIANT
<222> LOCATION: 3
<223> OTHER INFORMATION: Xaa=Phe, Trp, Tyr, Met or Leu
<220> FEATURE:
<221> NAME/KEY: VARIANT
<222> LOCATION: 5
<223> OTHER INFORMATION: Xaa=Leu, Ile or Val
<220> FEATURE:
<221> NAME/KEY: VARIANT
<222> LOCATION: 6
<223> OTHER INFORMATION: Xaa=Leu, Ile, Val or Thr
<220> FEATURE:
<221> NAME/KEY: VARIANT
<222> LOCATION: (7)...(7)
<223> OTHER INFORMATION: Xaa=Leu, Val or Met
<220> FEATURE:
<221> NAME/KEY: VARIANT
<222> LOCATION: (8)...(8)
<223> OTHER INFORMATION: xaa=Trp, Tyr, His, Thr or Met
<220> FEATURE:
<221> NAME/KEY: VARIANT
<222> LOCATION: (10)...(10)
<223> OTHER INFORMATION: Xaa=Leu, Ile, Val, Thr, Ala or Met
<220> FEATURE:
<221> NAME/KEY: VARIANT
<222> LOCATION: (11)...(11)
<223> OTHER INFORMATION: Xaa=Phe, Tyr, Leu, Ile, Thr, Val or Met

<400> SEQUENCE: 10

Xaa Xaa Xaa Gly Xaa Xaa Xaa Xaa Glu Xaa Xaa
 1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2
<223> OTHER INFORMATION: Xaa=Ala or Ser
<220> FEATURE:
<221> NAME/KEY: VARIANT
<222> LOCATION: 3
<223> OTHER INFORMATION: Xaa=Phe, Tyr,Met or Leu
<220> FEATURE:
<221> NAME/KEY: VARIANT
<222> LOCATION: 7
<223> OTHER INFORMATION: Xaa=Leu or Met
<220> FEATURE:
<221> NAME/KEY: VARIANT
```

```
<222> LOCATION: 8
<223> OTHER INFORMATION: Xaa=Tyr or Phe
<220> FEATURE:
<221> NAME/KEY: VARIANT
<222> LOCATION: 11
<223> OTHER INFORMATION: Xaa=Leu or Met

<400> SEQUENCE: 11

Trp Xaa Xaa Gly Val Leu Xaa Xaa Glu Met Xaa
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: xaa=Phe or Trp
<220> FEATURE:
<221> NAME/KEY: VARIANT
<222> LOCATION: 3
<223> OTHER INFORMATION: Xaa=Phe, Trp or Tyr
<220> FEATURE:
<221> NAME/KEY: VARIANT
<222> LOCATION: 5
<223> OTHER INFORMATION: Xaa=Val or Ile
<220> FEATURE:
<221> NAME/KEY: VARIANT
<222> LOCATION: 6
<223> OTHER INFORMATION: Xaa=Leu, Ile or Val
<220> FEATURE:
<221> NAME/KEY: VARIANT
<222> LOCATION: 10
<223> OTHER INFORMATION: Xaa=Leu or Val
<220> FEATURE:
<221> NAME/KEY: VARIANT
<222> LOCATION: (11)...(11)
<223> OTHER INFORMATION: Xaa=Leu or Ile

<400> SEQUENCE: 12

Xaa Ser Xaa Gly Xaa Xaa Leu Trp Glu Xaa Xaa
 1               5                  10

<210> SEQ ID NO 13
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 2
<223> OTHER INFORMATION: Xaa=Ala or Ser
<220> FEATURE:
<221> NAME/KEY: VARIANT
<222> LOCATION: 5,10
<223> OTHER INFORMATION: Xaa=Val or Ile
<220> FEATURE:
<221> NAME/KEY: VARIANT
<222> LOCATION: 11
<223> OTHER INFORMATION: xaa=Phe or Tyr

<400> SEQUENCE: 13

Trp Xaa Phe Gly Xaa Leu Met Trp Glu Xaa Xaa
 1               5                  10

<210> SEQ ID NO 14
<211> LENGTH: 11
<212> TYPE: PRT
<213> ORGANISM: Artificial Sequence
<220> FEATURE:
```

```
<223> OTHER INFORMATION: synthetic construct
<220> FEATURE:
<221> NAME/KEY: VARIANT
<222> LOCATION: 1
<223> OTHER INFORMATION: Xaa=Ser or Cys
<220> FEATURE:
<221> NAME/KEY: VARIANT
<222> LOCATION: 2
<223> OTHER INFORMATION: Xaa=Ser or Phe
<220> FEATURE:
<221> NAME/KEY: VARIANT
<222> LOCATION: 5
<223> OTHER INFORMATION: Xaa=Val or Ile
<220> FEATURE:
<221> NAME/KEY: VARIANT
<222> LOCATION: 6
<223> OTHER INFORMATION: Xaa=Gly or Gln
<220> FEATURE:
<221> NAME/KEY: VARIANT
<222> LOCATION: 7
<223> OTHER INFORMATION: Xaa=Phe or Cys
<220> FEATURE:
<221> NAME/KEY: VARIANT
<222> LOCATION: (8)...(8)
<223> OTHER INFORMATION: Xaa=Tyr or Phe
<220> FEATURE:
<221> NAME/KEY: VARIANT
<222> LOCATION: (10)...(10)
<223> OTHER INFORMATION: Xaa=Ala or Thr

<400> SEQUENCE: 14

Xaa Xaa Tyr Ile Xaa Xaa Xaa Xaa Gly Xaa Phe
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: synthetic construct

<400> SEQUENCE: 15

Tyr Ala Trp Ala Pro Lys Pro Tyr His Lys Phe
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 7
<223> OTHER INFORMATION: Xaa=Ile or Val
<220> FEATURE:
<221> NAME/KEY: VARIANT
<222> LOCATION: 10
<223> OTHER INFORMATION: Xaa=cys or Leu

<400> SEQUENCE: 16

Tyr Asp Tyr Arg Ser Ser Xaa Trp Ser Xaa Gly
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: Xaa=Ala, Lys or Tyr
```

-continued

```
<220> FEATURE:
<221> NAME/KEY: VARIANT
<222> LOCATION: 2
<223> OTHER INFORMATION: Xaa=Pro, His or Arg
<220> FEATURE:
<221> NAME/KEY: VARIANT
<222> LOCATION: 3
<223> OTHER INFORMATION: Xaa=Tyr, Phe or Trp
<220> FEATURE:
<221> NAME/KEY: VARIANT
<222> LOCATION: 4
<223> OTHER INFORMATION: xaa=Pro, Leu or Tyr
<220> FEATURE:
<221> NAME/KEY: VARIANT
<222> LOCATION: 6
<223> OTHER INFORMATION: Xaa=Lys, Ile or Ser
<220> FEATURE:
<221> NAME/KEY: VARIANT
<222> LOCATION: (8)...(8)
<223> OTHER INFORMATION: xaa=Phe or Tyr
<220> FEATURE:
<221> NAME/KEY: VARIANT
<222> LOCATION: (9)...(9)
<223> OTHER INFORMATION: Xaa=Asn, Asp or Pro
<220> FEATURE:
<221> NAME/KEY: VARIANT
<222> LOCATION: (11)...(11)
<223> OTHER INFORMATION: Xaa=Glu or Tyr

<400> SEQUENCE: 17

Xaa Xaa Xaa Xaa Arg Xaa Ala Xaa Xaa Ser Xaa
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 1
<223> OTHER INFORMATION: Xaa=Phe or Tyr
<220> FEATURE:
<221> NAME/KEY: VARIANT
<222> LOCATION: 2
<223> OTHER INFORMATION: Xaa=Ile, Val, Phe or Thr
<220> FEATURE:
<221> NAME/KEY: VARIANT
<222> LOCATION: 3
<223> OTHER INFORMATION: Xaa=Tyr, Arg, Leu, Lys or Gln
<220> FEATURE:
<221> NAME/KEY: VARIANT
<222> LOCATION: 8
<223> OTHER INFORMATION: Xaa=Cys, Trp or Tyr
<220> FEATURE:
<221> NAME/KEY: VARIANT
<222> LOCATION: 10
<223> OTHER INFORMATION: Xaa=Val or Leu
<220> FEATURE:
<221> NAME/KEY: VARIANT
<222> LOCATION: (11)...(11)
<223> OTHER INFORMATION: Xaa=Ala,Val or Ile

<400> SEQUENCE: 18

Xaa Xaa Xaa Ser Cys Ala Gly Xaa Cys Xaa Xaa
 1               5                  10

<210> SEQ ID NO 19
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
```

```
<222> LOCATION: 1
<223> OTHER INFORMATION: Xaa=Phe,Arg or Tyr
<220> FEATURE:
<221> NAME/KEY: VARIANT
<222> LOCATION: 4
<223> OTHER INFORMATION: Xaa=Glu, Phe or Ser
<220> FEATURE:
<221> NAME/KEY: VARIANT
<222> LOCATION: 5
<223> OTHER INFORMATION: Xaa=Lys, Tyr or His
<220> FEATURE:
<221> NAME/KEY: VARIANT
<222> LOCATION: 7
<223> OTHER INFORMATION: Xaa=Tyr, Phe or His
<220> FEATURE:
<221> NAME/KEY: VARIANT
<222> LOCATION: 10
<223> OTHER INFORMATION: Xaa=Phe, His, Asn or Val
<220> FEATURE:
<221> NAME/KEY: VARIANT
<222> LOCATION: (11)...(11)
<223> OTHER INFORMATION: Xaa=Lys, Ser, Asn or Thr

<400> SEQUENCE: 19

Xaa Leu Trp Xaa Xaa Arg Xaa Tyr Cys Xaa Xaa
 1               5                   10
```

US 8,058,227 B2

METHOD OF TREATING FIBROSIS IN A SUBJECT IN NEED THEREOF COMPRISING ADMINISTERING A COMPOSITION COMPRISING A CSD

This application claims the benefit of U.S. Provisional Application 60/828,009, filed on Oct. 3, 2006 which is incorporated herein in its entirety.

This invention was funded by R01 HL73718 from the NHLBI, National Institutes of Health, and NIH/NCRR facilities construction grant No. C06 RR015455. The government has certain rights in the invention.

I. BACKGROUND

Scleroderma is a debilitating disease characterized by immune system activation and autoimmunity, small-vessel vasculopathy, and fibrosis of the skin, lungs and other organs. It affects approximately 100,000 people in the US, mostly women. The major cause of morbidity and mortality in scleroderma is pulmonary fibrosis (55,56), i.e. the excessive accumulation in the lungs of extracellular matrix (ECM) proteins, particularly collagen. The cell type most frequently associated with fibrosis is the myofibroblast. Myofibroblasts are fibroblasts that exhibit certain muscle-like properties: they are contractile and they contain the marker protein α-smooth muscle actin (ASMA) (5). There are few myofibroblasts in normal lung tissue. In contrast, there are many more fibroblasts in fibrotic lung tissue than in normal tissue. Many of these fibroblasts are myofibroblasts, and collagen deposition in fibrotic lung tissue routinely occurs at sites rich in myofibroblasts. Thus it is clear that these cells play a key role in the genesis of fibrotic lesions.

II. SUMMARY

Disclosed are methods and compositions related to in one aspect treatment of fibrosis. Also disclosed are methods of screening for agents for the treatment of fibrosis.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows that CSD peptide inhibits collagen expression and MEK/ERK activation. NLF and SLF were treated with either the CSD peptide (+) or scrambled peptide (−). The levels of collagen in the culture medium and of PKCα, PKCε, ph-MEK, ph-ERK, total MEK, total ERK, caveolin-1, and actin in the cell layer were determined by Western blotting and quantified densitometrically. The results of a representative Western blotting experiment are shown in FIG. 1A. Densitometric analyses (average±s.e.m.) combining the results of three independent experiments performed with three distinct strains of NLF and SLF are shown in FIG. 1B. No changes in actin (loading control) were observed. The level of each protein present in control NLF cultures was defined as 100 arbitrary units. Statistical significance: ***$p<0.001$.

Figure 2:
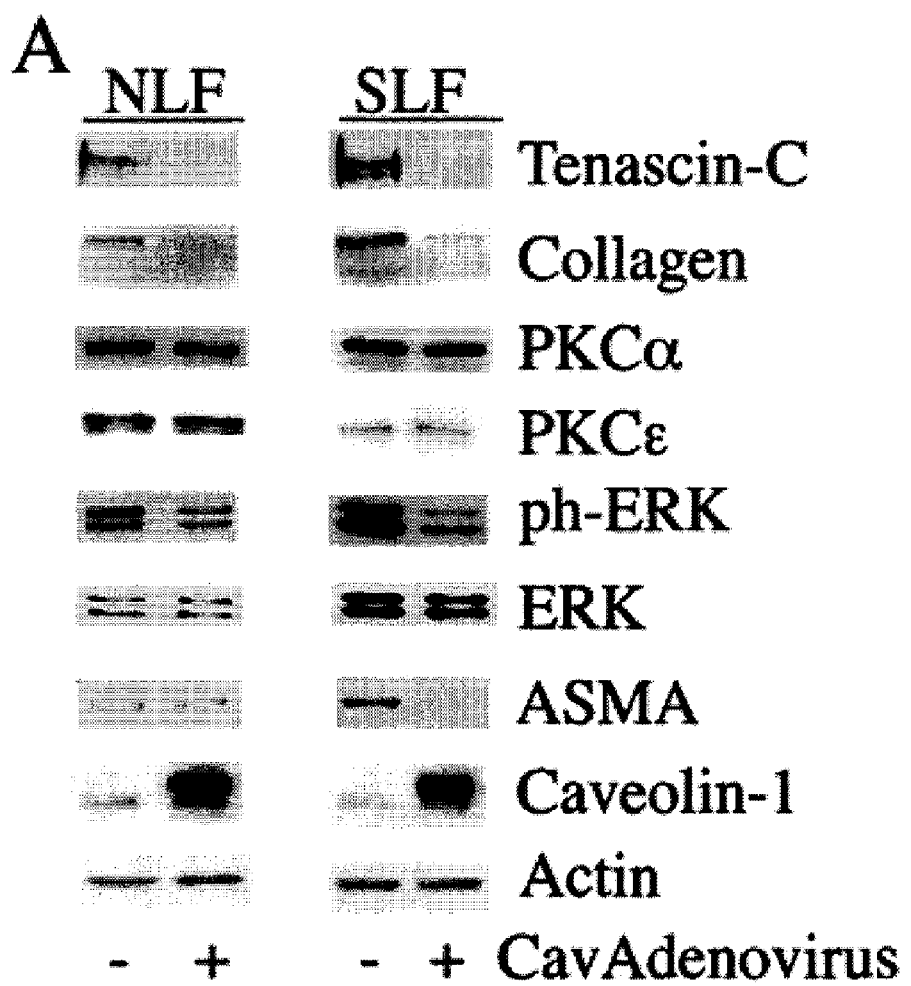
Figure 2:
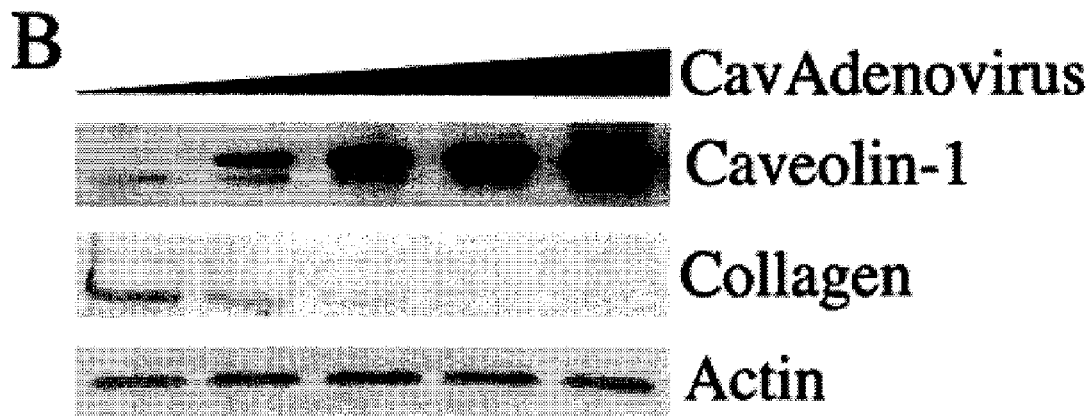

FIG. 2 shows that Caveolin-1 adenovirus inhibits collagen and tenascin-C expression and ERK activation. FIG. 2A shows that NLF and SLF were infected with adenovirus encoding full-length caveolin-1 (CavAdenovirus+) or with empty virus (−). The levels of tenascin-C and collagen in the culture medium and of PKCα, PKCε, ph-ERK, ERK, ASMA, caveolin-1, and actin (loading control) in the cell layer were determined by Western blotting. The high level of caveolin-1 detected in + cells confirms the success of this treatment. The results of a representative Western blotting experiment are shown. Similar results were obtained in three independent experiments performed with distinct strains of NLF and SLF. Statistical significance: SLF express higher levels of tenascin-C, collagen, ph-ERK, and ASMA than NLF and lower levels of PKCε, $p<0.001$. Caveolin-1 overexpression in both NLF and SLF results in lower expression of tenascin-C, collagen, and ph-ERK, $p<0.001$. Caveolin-1 overexpression has no effect on ASMA expression in NLF, but lowers ASMA expression in SLF, $p<0.001$. FIG. 2B shows that NLF were infected with increasing volumes of CavAdenovirus (0, 1, 2, 5, 10 μl) prepared as described by Pannu et al. (24). The levels of collagen in the culture medium and caveolin-1 and actin (loading control) in the cell layer were determined by Western blotting. The results of a representative experiment are shown. Similar results were obtained with three distinct strains of NLF and with three distinct strains of SLF.

Figure 3:
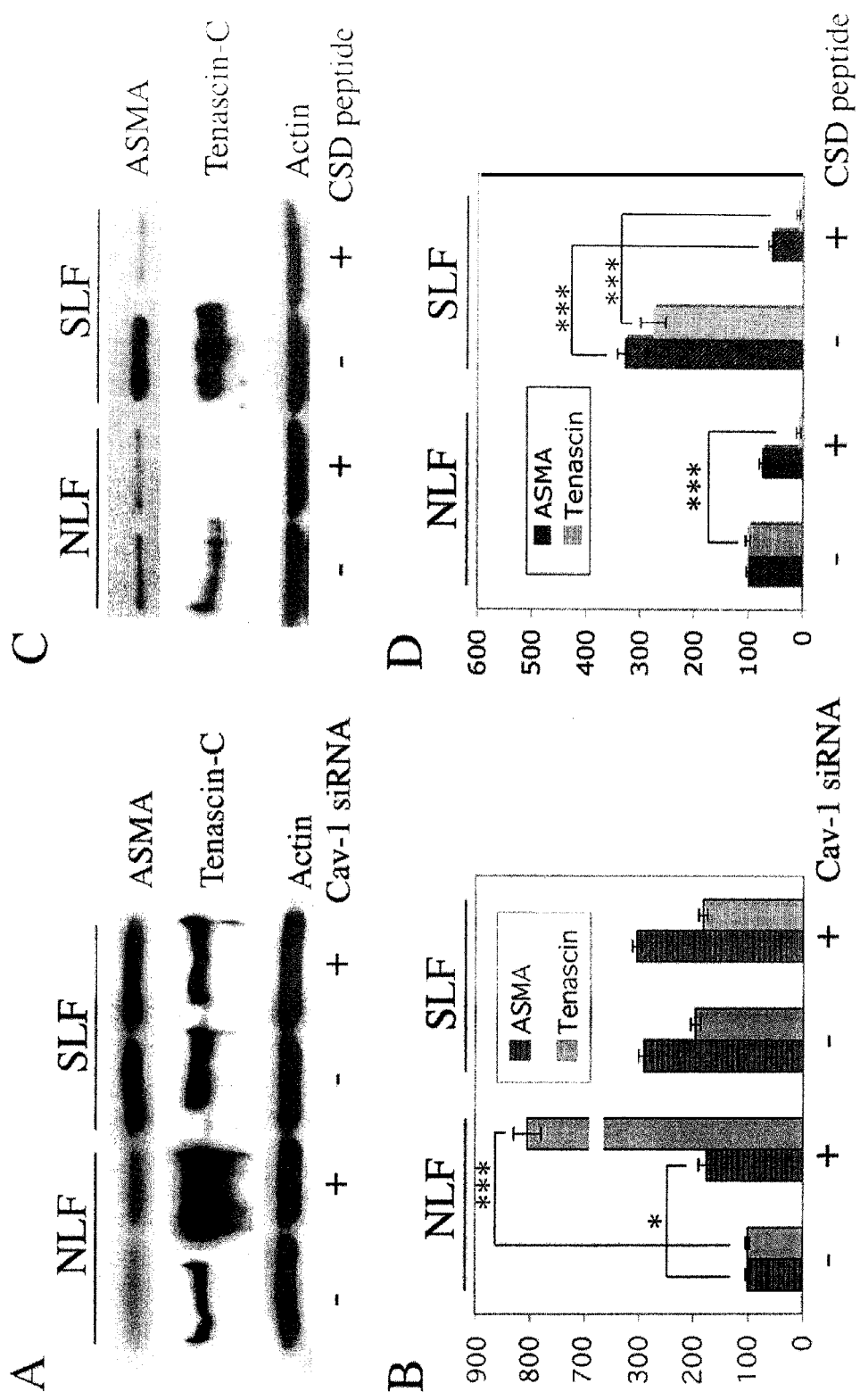

FIG. 3 shows the regulation of ASMA and tenascin-C expression by caveolin-1. Tenascin-C in the culture medium and ASMA and actin in the cell layer were detected by Western blotting and quantified densitometrically. FIGS. 3A and 3B show that NLF and SLF were transfected with synthetic double-stranded caveolin-1 siRNA (+) or were mock-transfected (−). The results of a representative Western blotting experiment are shown in FIG. 3A. Densitometric analyses (average±s.e.m.) combining the results of three independent experiments performed with three distinct strains of NLF and SLF are shown in FIG 3B. No changes in actin (loading control) were observed. FIGS. 3C and 3D shows that NLF and SLF were treated with either the CSD peptide (+) or scrambled peptide (−). The results of a representative Western blotting experiment are shown in FIG. 3C. Densitometric analyses (average±s.e.m.) combining the results of three independent experiments performed with three distinct strains of NLF and SLF are shown in FIG. 3D. No changes in actin (loading control) were observed. The level of each protein present in control NLF cultures was defined as 100 arbitrary units. Statistical significance: *$p<0.05$; ***$p<0.001$.

Figure 4:
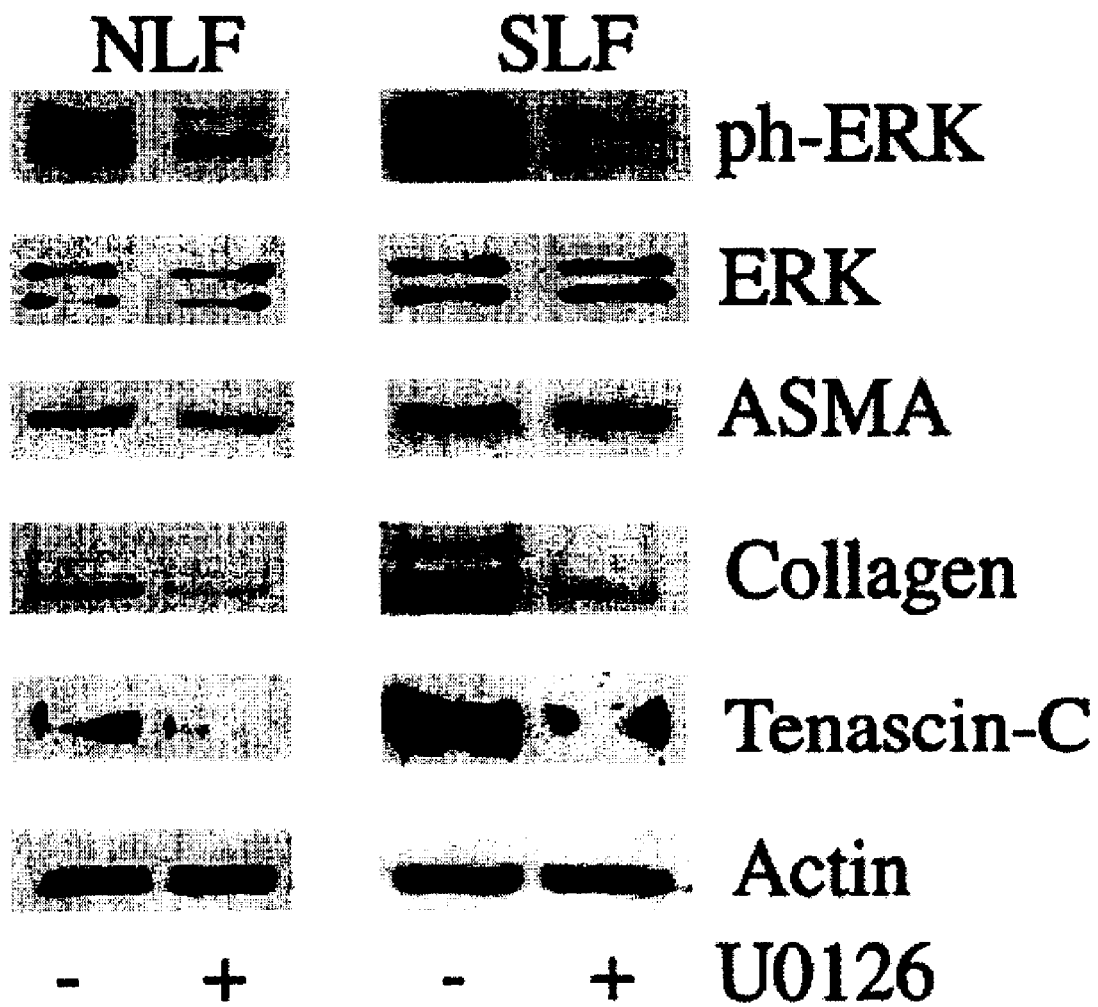

FIG. 4 shows that collagen and Tenascin-C expression, but not ASMA expression, is regulated by MEK/ERK signaling. NLF and SLF were incubated in the presence (+) or absence (−) of the MEK inhibitor U0126. Levels of collagen and tenascin-C in the culture medium and ph-ERK, ERK, ASMA, and actin (loading control) in the cell layer were detected by Western blotting. Similar results were obtained in three independent experiments performed with three distinct strains of NLF and SLF. Statistical significance: U0126 inhibits the expression of collagen, tenascin-C, and ph-ERK in both NLF and SLF, $p<0.001$.

Figure 5:
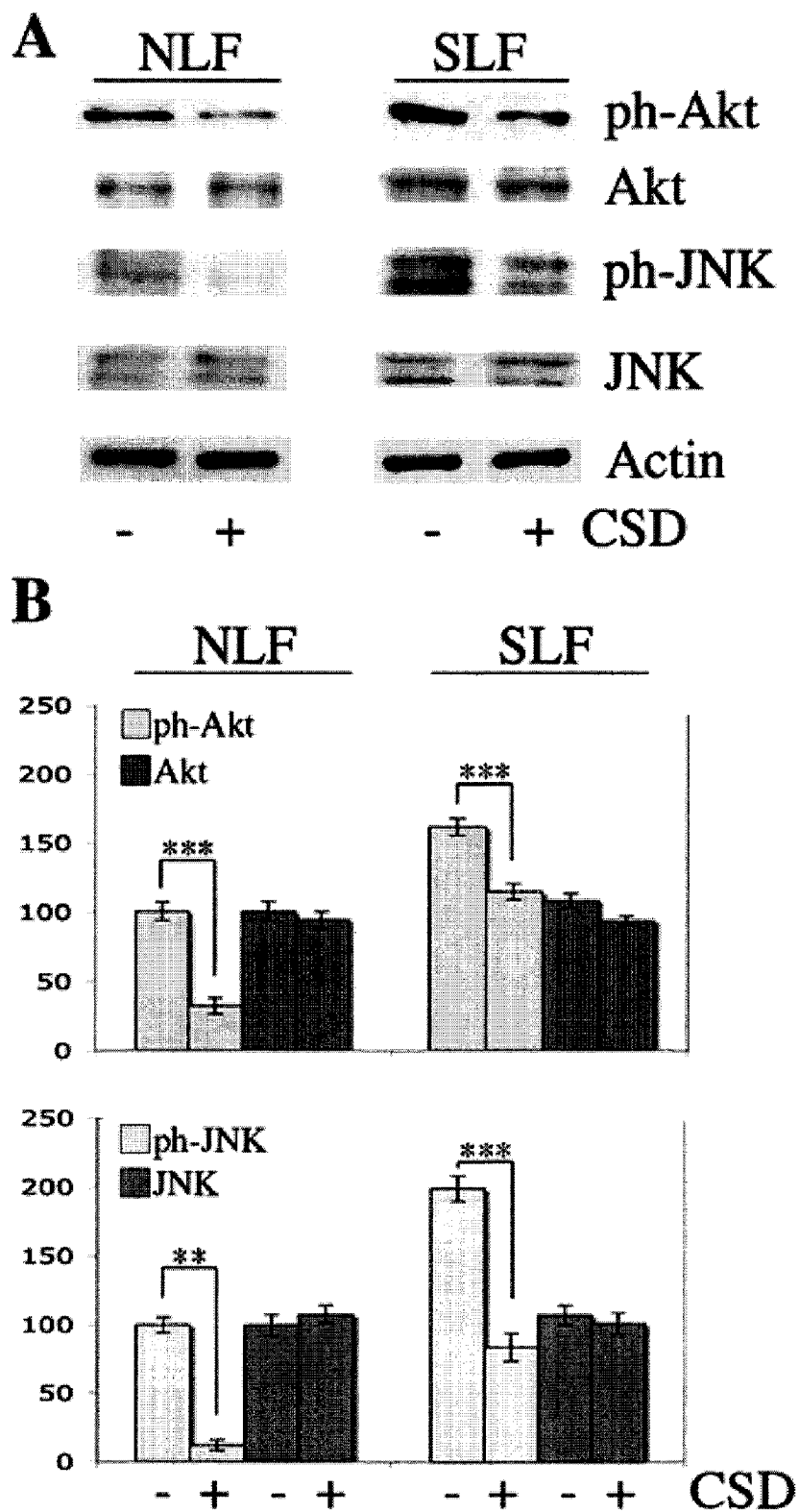

FIG. 5 shows that expression of activated Akt and JNK in NLF and SLF treated with the CSD peptide. NLF and SLF were treated with either the CSD peptide (+) or scrambled peptide (−). Ph-Akt, ph-JNK, total Akt, total JNK, and actin in the cell layer were determined by Western blotting and quantified densitometrically. The results of a representative Western blotting experiment are shown in FIG. 5A. Densitometric analyses (average±s.e.m.) combining the results of three independent experiments performed with three distinct strains of NLF and SLF are shown in FIG. 5B. No changes in actin (loading control) were observed. The level of each protein present in control NLF cultures was defined as 100 arbitrary units. Statistical significance: $p<0.01$; *$p<0.001$.

Figure 6:
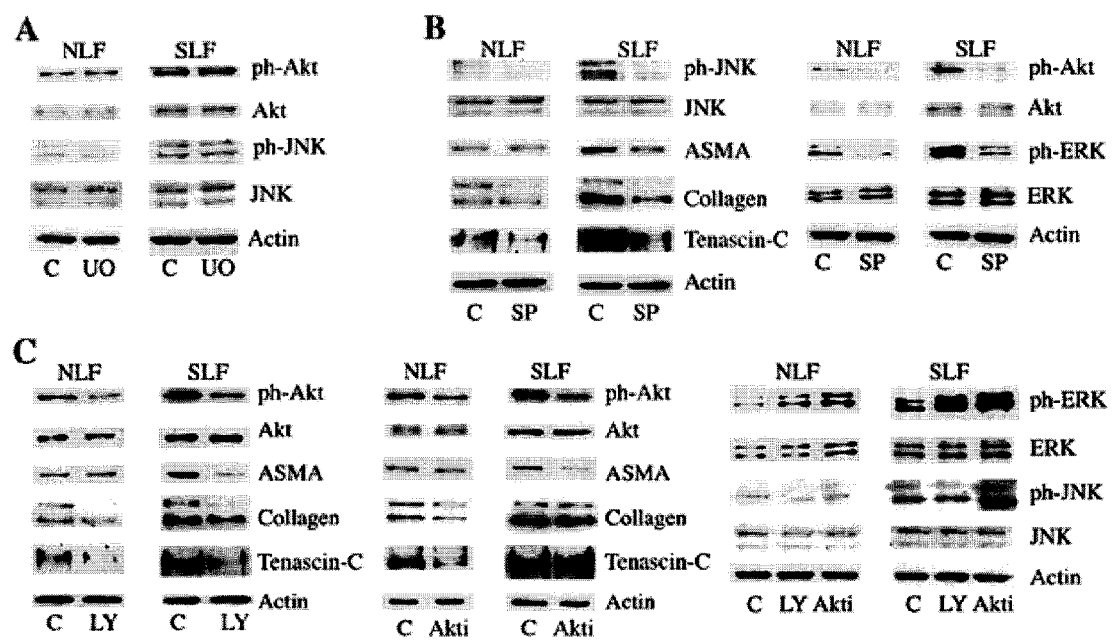

FIG. 6 shows the effects of signaling inhibitors on collagen, tenascin-C, and ASMA expression and on cross-talk between signaling proteins. NLF and SLF were incubated in the absence (C) or presence of U0126 (UO), SP600125 (SP), LY294002 (LY), or Akt inhibitor VIII (Akti). Collagen and tenascin-C in the medium and ph-Akt, ph-ERK, total Akt, total JNK, total ERK, ASMA, and actin (loading control) in the cell layer were detected by Western blotting. FIG. 6A shows the effects of U0126. FIG. 6B shows the effects of SP600125. FIG. 6C shows the effects of LY294002 and Akt inhibitor VIII. Similar results were obtained in three independent experiments performed with three distinct strains of NLF and SLF. Statistical significance: SP600125 inhibits the expression in NLF of ph-JNK ($p<0.01$), tenascin-C ($p<0.001$), ph-Akt ($p<0.05$), and ph-ERK ($p<0.01$). SP600125 inhibits the expression in SLF of ph-JNK, collagen, tenascin-C, ph-Akt, ph-ERK (all $p<0.001$) and ASMA ($p<0.01$). LY294002 inhibits the expression in NLF of ph-Akt ($p<0.001$), collagen ($p<0.01$), and tenascin-C ($p<0.05$) and promotes the expression of ph-ERK ($p<0.05$). LY294002 inhibits the expression in SLF of ph-Akt, ASMA, collagen, and tenascin-C and promotes the expression ph-ERK (all $p<0.001$). Akt inhibitor VIII inhibits the expression in NLF of ph-Akt, collagen, and tenascin-C and promotes the expression of ph-ERK (all $p<0.01$). Akt inhibitor VIII inhibits the expression in SLF of ph-Akt and ASMA and promotes the expression of ph-ERK and ph-JNK (all $p<0.001$).

Figure 7:
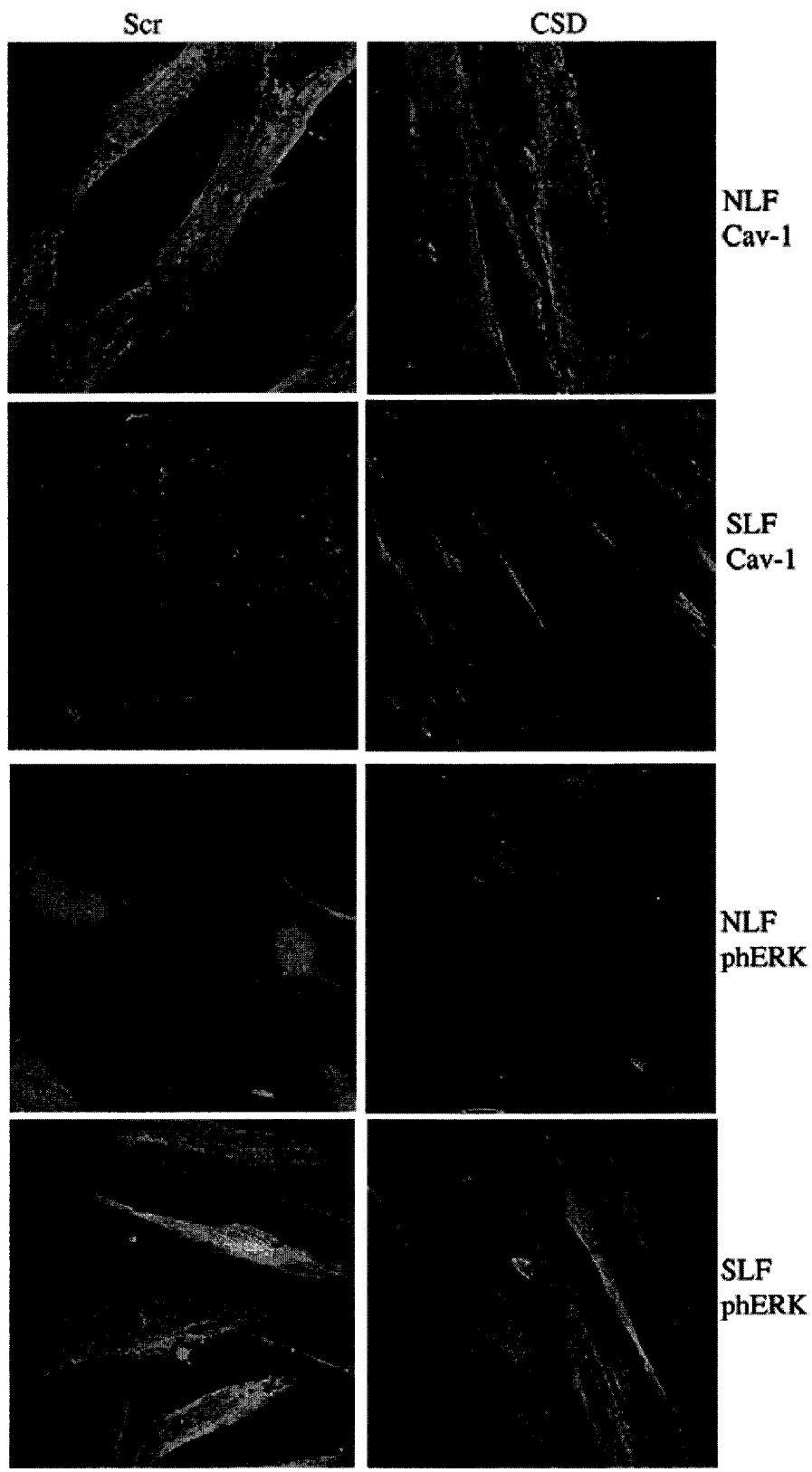

FIG. 7 shows that CSD peptide treatment alters the subcellular localization of caveolin-1 and ph-ERK. NLF or SLF cultured in 4-well glass chamber slides (Nalge Nunc International, Naperville, Ill.) as previously described (43) were incubated with CSD peptide or scrambled (Scr) peptide, fixed, permeabilized, and stained red with 7-aminoactinomycin D to detect nuclei and green using appropriate primary and secondary antibodies to detect caveolin-1 or ph-ERK. Images were captured by confocal microscopy.

Figure 8:
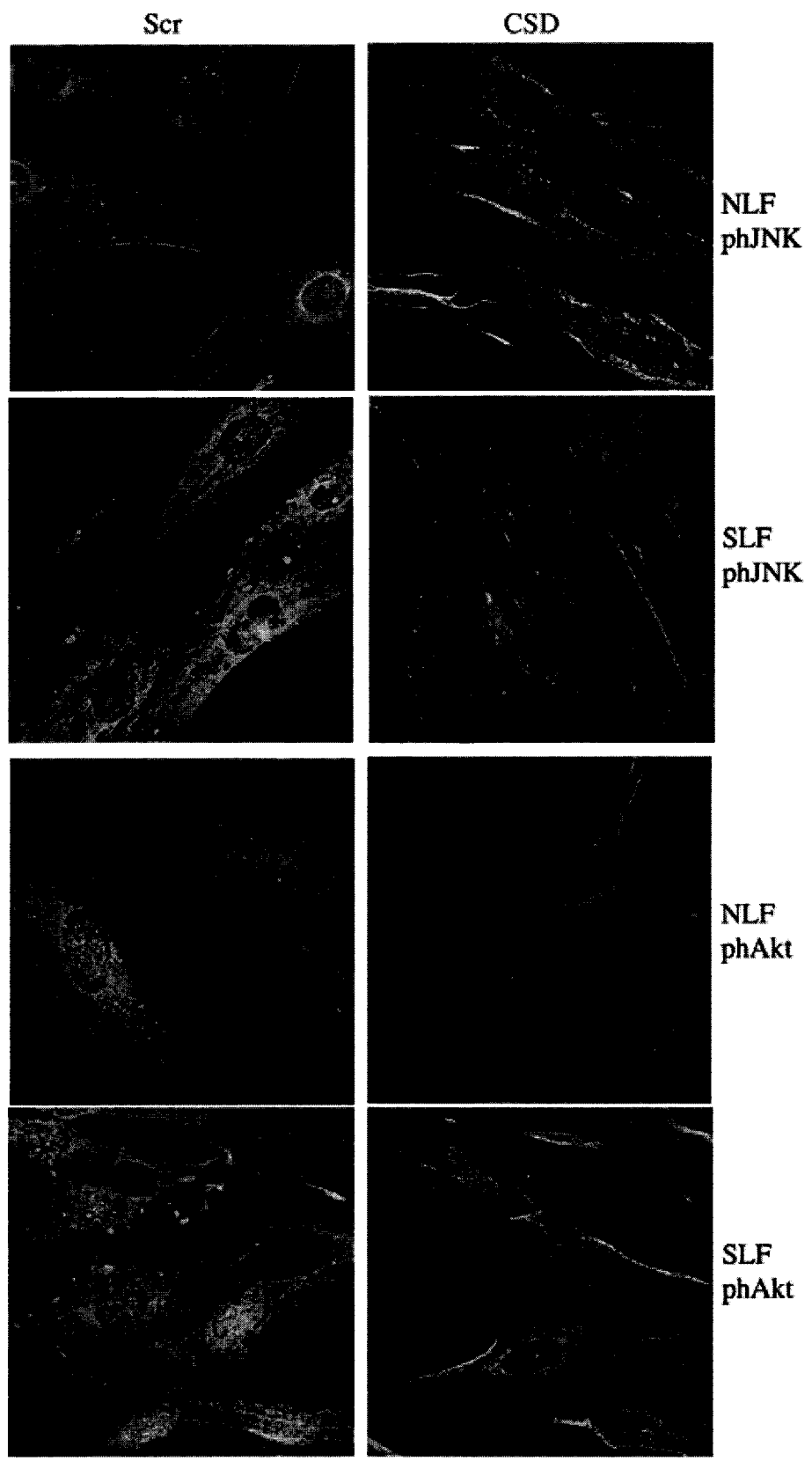

FIG. 8 shows that CSD peptide treatment alters the subcellular localization of ph-JNK and ph-Akt. NLF or SLF cultured in 4-well glass chamber slides (Nalge Nunc International, Naperville, Ill.) as previously described (43) were incubated with CSD peptide or scrambled (Scr) peptide, fixed, permeabilized, and stained red with 7-aminoactinomycin D to detect nuclei and green using appropriate primary and secondary antibodies to detect ph-JNK or ph-Akt. Images were captured by confocal microscopy.

Figure 9:
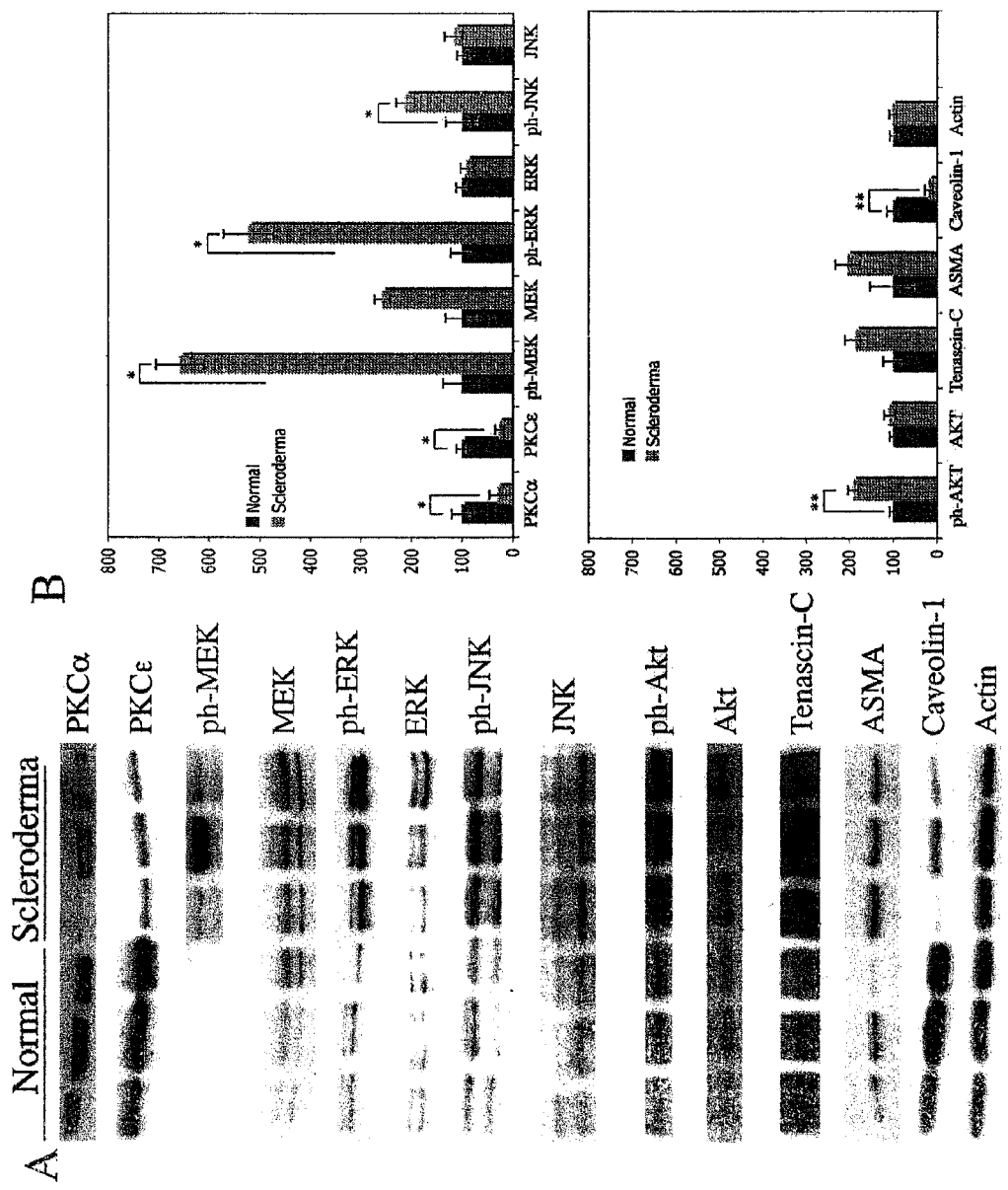

FIG. 9 shows the quantification of signaling proteins, tenascin-C, and ASMA in control and fibrotic human lung tissue. Adult human lung tissue obtained at autopsy from three normal subjects and three scleroderma patients was dissolved in SDS-PAGE sample buffer; analyzed by Western blotting (25 µg total protein per lane) using antibodies against PKCα, PKCε, ph-MEK, total MEK, ph-ERK, total ERK, ph-JNK, total JNK, ph-Akt, total Akt, tenascin-C, ASMA, caveolin-1, and actin (loading control); and the results quantified densitometrically. The results of a representative Western blotting experiment are shown in FIG. 9A. Densitometric analyses (average±s.e.m.) combining the results of the three independent experiments are shown in FIG. 9B. No changes in actin (loading control) were observed. The level of each protein present in normal lung tissue was defined as 100 arbitrary units. Statistical significance: *$p<0.05$; **$p<0.01$.

Figure 10:
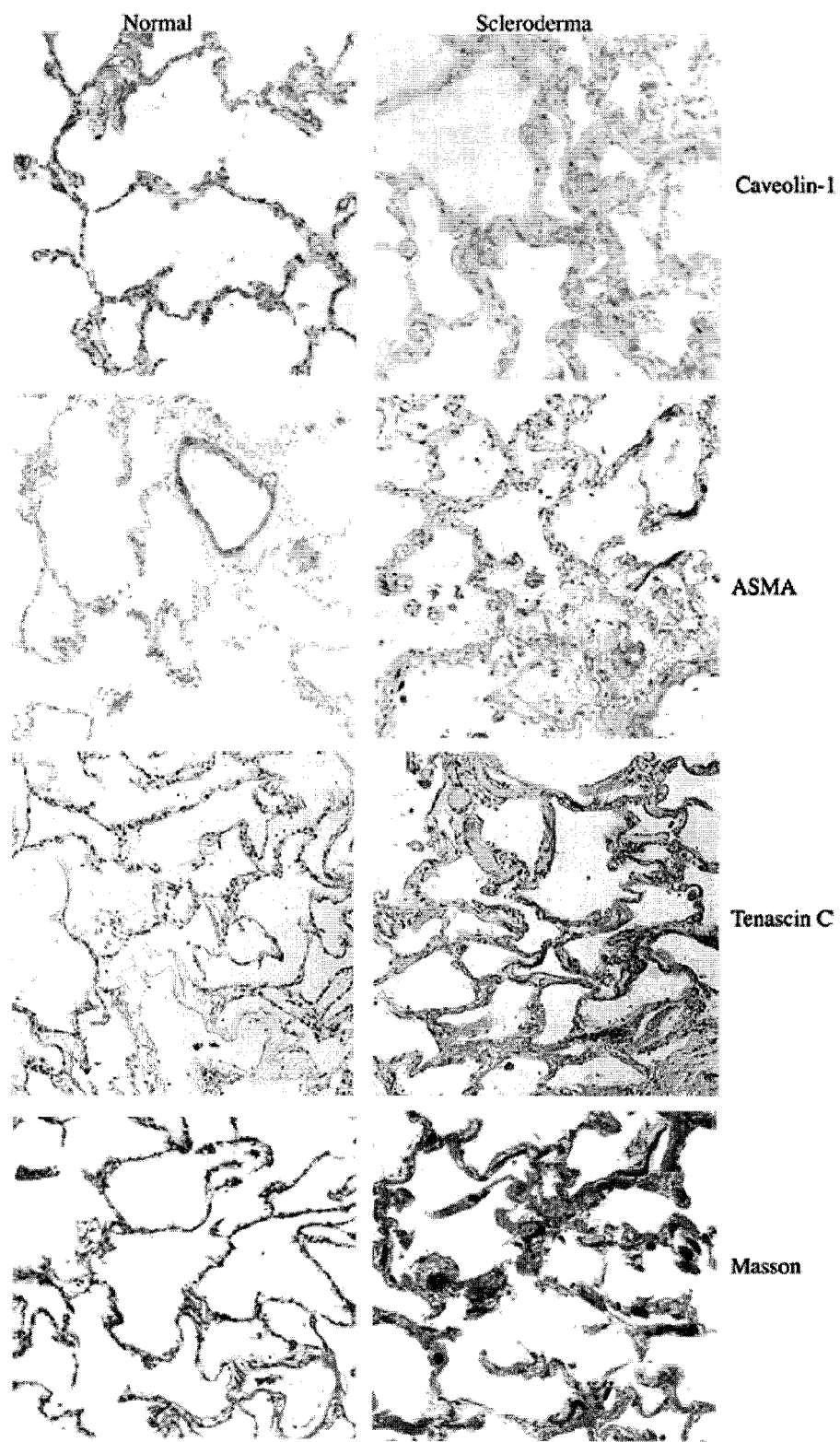

FIG. 10 shows that localization of caveolin-1, ASMA, tenascin-C, and collagen in normal and fibrotic human lung tissue. Fixed, paraffin-embedded tissue sections from Normal and Scleroderma adult human lung tissue were stained for Caveolin-1, ASMA, and Tenascin-C using the primary antibodies described in the Methods. Development of the color reaction (brown product) was accomplished using appropriate HRP-conjugated secondary antibodies and DAB substrate and counterstaining with hematoxylin. Collagen was detected using Masson's Trichrome stain (blue reaction product). Similar results were obtained in three independent experiments using tissue from three normal subjects and three scleroderma patients.

Figure 11:
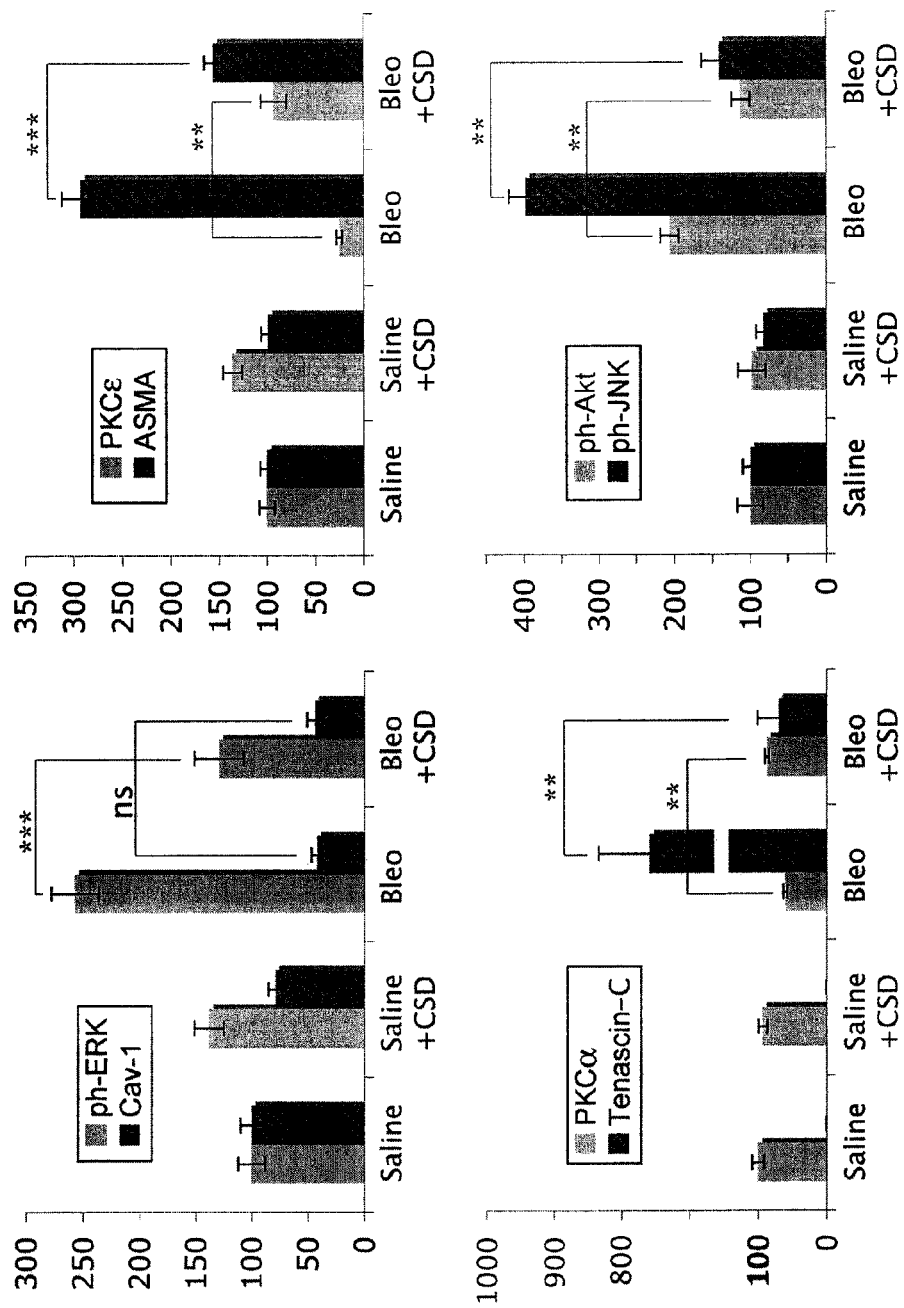

FIG. 11 shows the effects of Bleomycin-Induced Fibrosis and CSD peptide treatment on the expression of signaling molecules, tenascin-C, and ASMA in mouse lung tissue. As described in the Methods, lung tissue from the following mice was dissolved in SDS-PAGE sample buffer: saline-treated mice that did not receive the CSD peptide (Saline), saline-treated mice that received the CSD peptide via Alzet pumps or intraperitoneal injection (Saline+CSD), bleomycin-treated mice that did not receive the CSD peptide (Bleo), and bleomycin-treated mice that received the CSD peptide via Alzet pumps or intraperitoneal injection (Bleo+CSD). Extract from each mouse was analyzed by Western blotting (25 µg total protein per lane) using antibodies against ph-ERK, caveolin-1, PKCε, ASMA, PKCα, tenascin-C, ph-Akt, ph-JNK, and actin (loading control); and the results quantified densitometrically (averages±s.e.m. are shown). The level of each protein in "Saline" was set to 100 arbitrary units. Actin levels (loading control) were similar in all four samples (not shown). Statistical significance: ns, not significant; $p<0.01$; *$p<0.001$.

Figure 12:
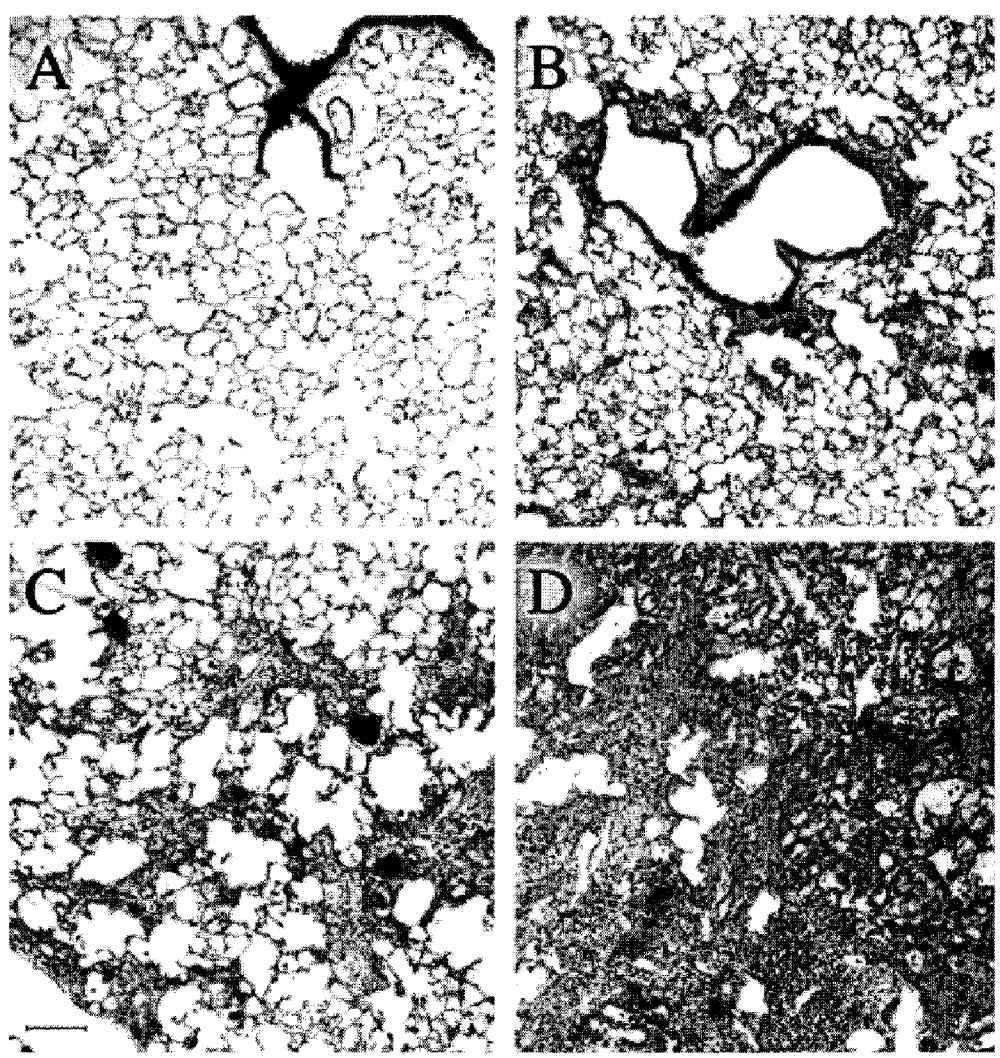

FIG. 12 shows the effects of bleomycin and the CSD peptide on collagen expression and lung tissue morphology. Masson's Trichrome-stained sections from the experiments described in FIG. 11 were used to evaluate the effects of bleomycin and the CSD peptide on collagen expression (blue product) and lung tissue morphology. A through D are representative sections of: FIG. 12A shows no pump, intratracheal saline—normal lung tissue; FIG 12B shows CSD peptide pump, intratracheal bleomycin—slight tissue damage and collagen over-expression; FIG. 12C shows CSD peptide pump, intratracheal bleomycin—moderate tissue damage and collagen over-expression; FIG. 12D shows No pump, intratracheal bleomycin—severe tissue damage and collagen over-expression. To generate the table, Masson's Trichrome-stained slides of lung tissue from all 41 mice sacrificed 14 days after saline or bleomycin treatment were scored blind in terms of the portion of the lung with abnormal morphology using an arbitrary scale: Normal morphology as in A=0, slightly altered morphology as in B=1, moderately altered morphology as in C=2, and severely altered morphology as in D 3. Mice that died prior to 14 days after bleomycin treatment are also indicated in the table. Bar in C=0.1 mm.

Figure 13:
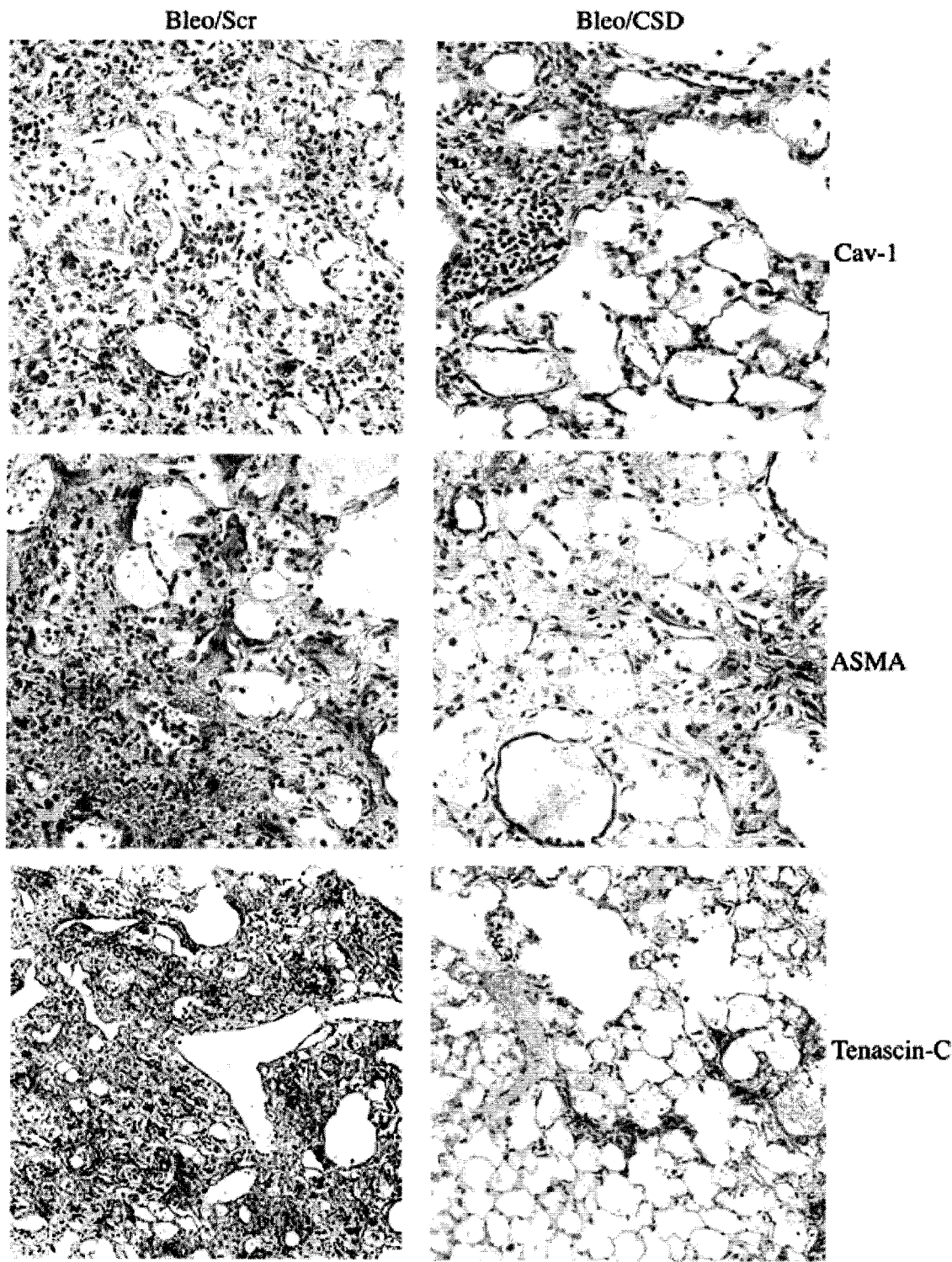

FIG. 13 shows the effect of CSD peptide treatment on the localization of caveolin-1, ASMA, and tenascin-C in bleomycin-treated mice. Fixed, paraffin-embedded tissue sections from bleomycin-treated mice that received CSD peptide (Bleo/CSD) or that received the scrambled, control peptide (Bleo/Scr) were stained for Caveolin-1, ASMA, and Tenascin-C using the primary antibodies described in the Methods. Development of the color reaction (brown product) was accomplished using appropriate HRP-conjugated secondary antibodies and DAB substrate and counterstaining with hematoxylin. Similar results were obtained in three independent experiments using distinct bleomycin-treated mice receiving either the CSD peptide or the scrambled, control peptide.

Figure 14:
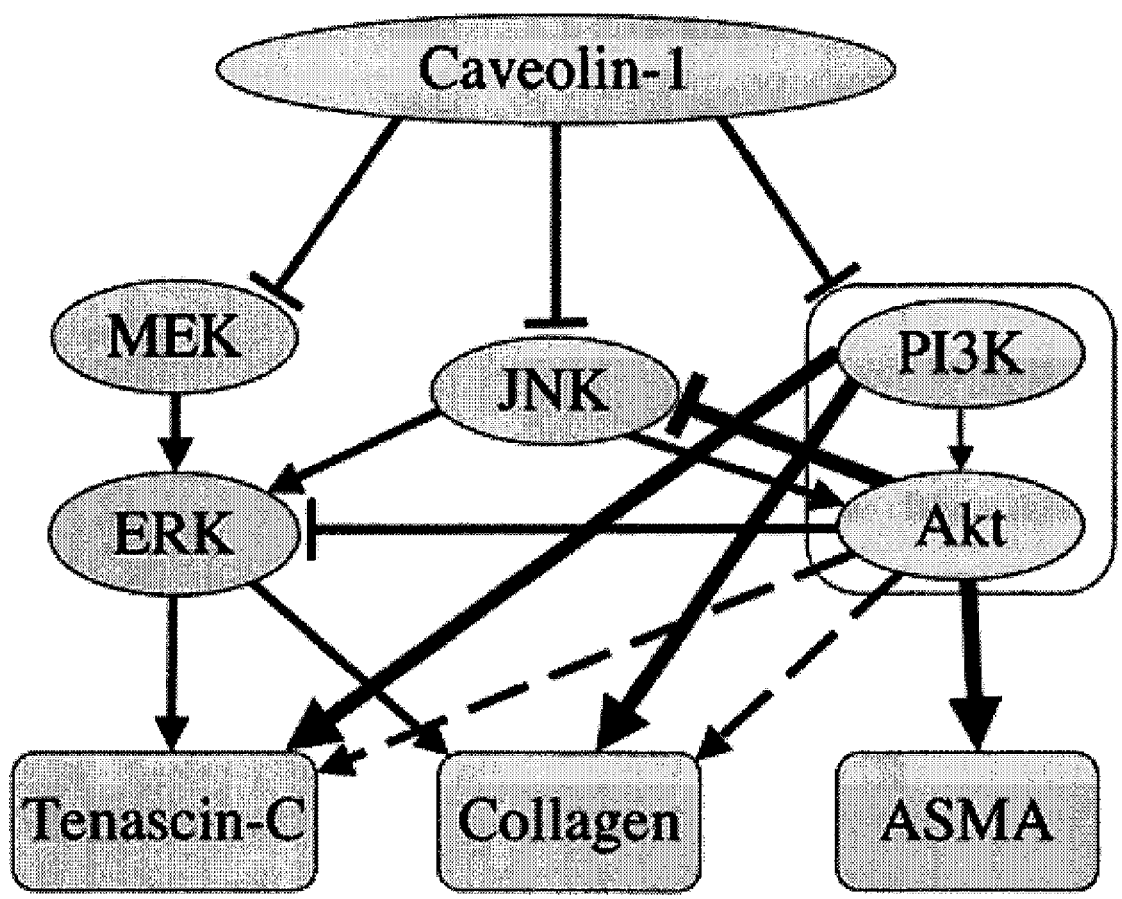

FIG. 14 shows the regulation of collagen, tenascin-C, and ASMA expression in lung fibroblasts by Caveolin-1, MEK, ERK, JNK, PI3K, and Akt. Thin lines are pathways observed in both NLF and SLF. Thick lines are pathways observed only in SLF. Dashed lines are pathways observed only in NLF.

Figure 15:
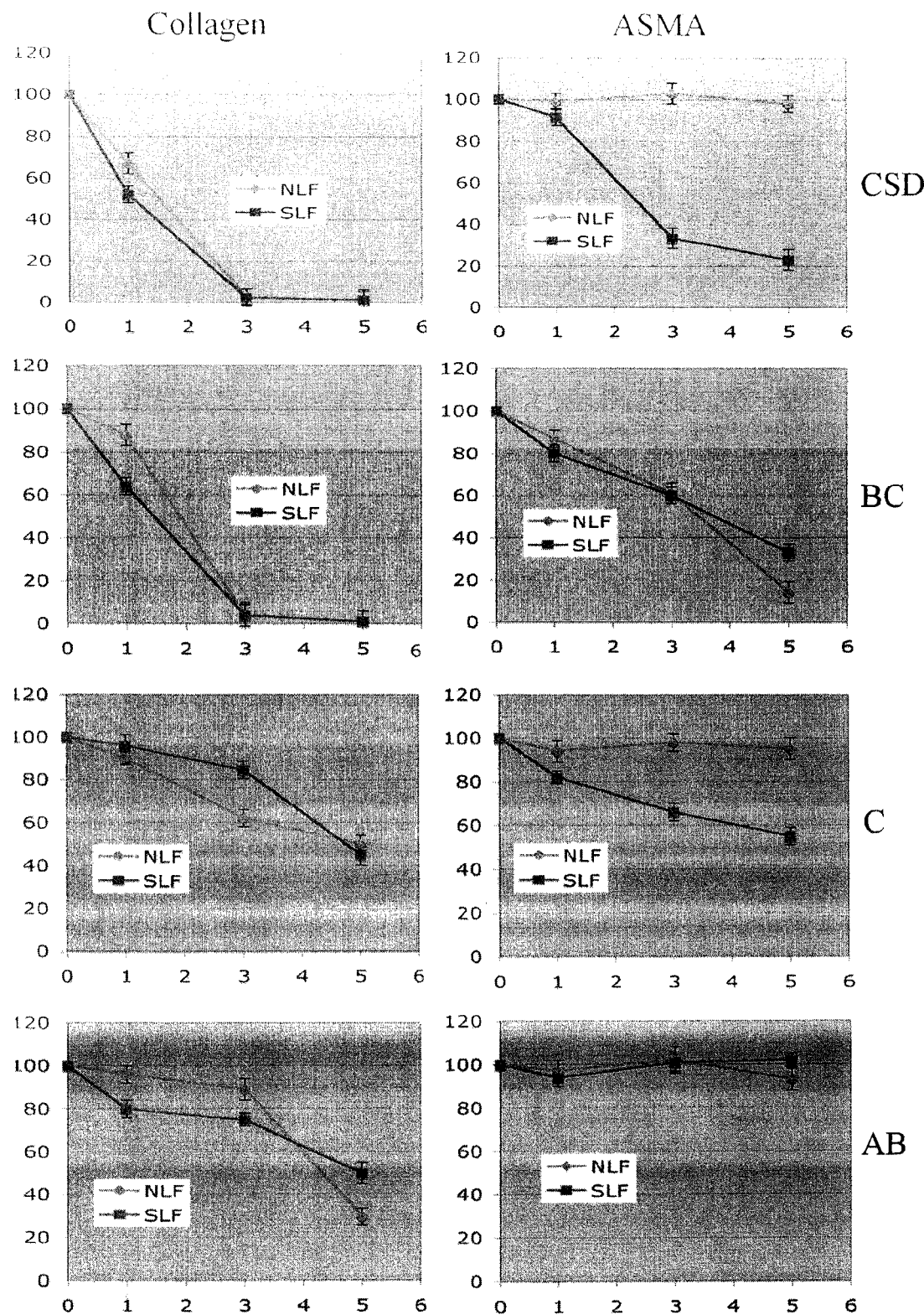

FIG. 15 shows the collagen and ASMA expression in peptide-treated cells. The indicated cell types (NLF and SLF)

were cultured as described with 0, 1, 3, or 5 μM of the indicated peptides. Collagen in the medium and ASMA and actin (loading control) in the cell layer were detected by Western blotting. Blots were quantified densitometrically. The level of collagen and ASMA in cells treated with no peptide (divided by the level of actin) was set to 100 arbitrary units. Because SLF express higher levels of collagen and ASMA than do NLF, 100 arbitrary of collagen in SLF is equivalent to 195 arbitrary units of collagen in NLF and 100 arbitrary units of ASMA in SLF is equivalent to 255 arbitrary units of ASMA in NLF. The data presented are the average of the densitometric quantification of three independent experiments.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "decrease" can refer to any change that results in a smaller amount of a symptom, composition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed.

An "increase" can refer to any change that results in a larger amount of a symptom, composition, or activity. Thus, for example, an increase in the amount of CSD can include but is not limited to a 10%, 20%, 30%, 40%, 50%, 60%, 70%, 80%, 90%, or 100% increase.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Enhance," "enhancing," and "enhamcement" mean to increase an activity, response, condition, disease, or other biological parameter. This can include but is not limited to the doubling, tripling, quadrupling, or any other factor of increase in activity, response, condition, or disease. This may also include, for example, a 10% increase in the activity, response, condition, or disease as compared to the native or control level. Thus, the increase can be a 10, 20, 30, 40, 50, 60, 70, 80, 90, 100, 150, 200, 300, 400, 500% or any amount of increase in between as compared to native or control levels.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Methods Of Treatment

Fibrosis involves the overexpression of extracellular matrix (ECM) proteins, primarily collagen, by α-smooth muscle actin (ASMA)-positive cells. Caveolin-1 is a master regulator of collagen expression by lung fibroblasts in vitro and of lung fibrosis in vivo. A peptide equivalent to the caveolin-1 scaffolding domain (CSD peptide) inhibits collagen and tenascin-C expression by normal lung fibroblasts (NLF) and fibroblasts from the fibrotic lungs of scleroderma patients (SLF). CSD peptide inhibits ASMA expression in SLF, but not NLF. Similar inhibition of collagen, tenascin-C, and ASMA expression was also observed when caveolin-1 expression was up-regulated using adenovirus. These observations indicate that the low caveolin-1 levels in SLF cause their overexpression of collagen, tenascin-C, and ASMA. Systemic administration of CSD peptide to bleomycin-treated mice blocks changes in tissue morphology; signaling molecule activation; and collagen, tenascin-C, and ASMA expression associated with lung fibrosis. Therefore, disclosed herein are methods of treating fibrosis in a subject in need thereof comprising administering to the subject a composition comprising a caveolin-1 scaffolding domain (CSD) moiety or a fragment, derivative, or analogue thereof.

Treatment," "treat," or "treating" mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, "treatment" can refer to a 10%, 20%, 30%, 40%, 50%, 60%, 70%, 80%, 90%, or 100% reduction in the severity of an established disease or the disease progression. For example, a disclosed method for reducing the effects of fibrosis is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition.

1. Caveolin-1

Caveolin-1, the principal coat protein of caveolae, is a promising therapeutic target for treating lung fibrosis (44,50). Caveolae were originally observed in electron microscopic images as flask-shaped invaginations in the plasma membrane. These cholesterol- and sphingolipid-rich organelles function in endocytosis, vesicular trafficking, and in the compartmentalization of specific signaling cascades (1). The caveolin family of caveolae coat proteins contains three members. Caveolin-1 and -2 are abundantly expressed in adipocytes, endothelial cells, and fibroblasts; caveolin-3 is muscle specific (31,36). Caveolins serve as scaffolds for signaling molecules including members of the MAP kinase family, isoforms of PKC, Akt, G proteins, Src-family kinases, and growth factor receptors (9,19,29,30,32,33). The interaction of kinases with caveolins frequently inhibits their activity (22). Conversely, caveolin-1 depletion hyperactivates signaling molecules both in vitro (13,44) and in vivo (8).

There are extensive observations linking caveolin-1 to the regulation of collagen expression in vitro and the progression of lung fibrosis in vivo. High levels of caveolin-1 are found in NLF, whereas much lower levels are found in SLF and in fibroblasts from the fibrotic lung tissue of IPF patients (49, 50). This difference in caveolin-1 levels appears to be responsible for the overexpression of collagen in cells from fibrotic tissue because when caveolin-1 expression is knocked down in NLF using siRNA, collagen expression increases dramatically (44). Conversely, adenovirus-mediated caveolin-1 overexpression inhibits TGFβ-induced collagen and fibronectin expression (50). In vivo, two groups observed that in caveolin-1 null mice lung tissue shows significant pathology: the diameter of alveolar spaces is reduced, alveolar walls are thickened and hypercellular, and ECM deposition is significantly increased (11,28). Similarly, caveolin-1 levels are strikingly decreased in lung tissue induced to become fibrotic by irradiation or by bleomycin treatment (17,44), and in fibrotic lung tissue from human IPF patients (50). Finally, intratracheal administration of adenovirus mediating the overexpression of caveolin-1 (50) blocks the progression of bleomycin-induced lung fibrosis in mice. Thus, there is a clear cut causal relationship between low caveolin-1 levels and lung fibrosis.

The ability of caveolin-1 to bind to a variety of kinases and thereby inhibit their activity has been mapped to a sequence known as the caveolin-1 scaffolding domain (CSD, amino acids 82-101 of caveolin-1) (23). A peptide equivalent to the CSD can cross the plasma membrane when synthesized as a fusion peptide on the C terminus of the Antennapedia internalization sequence (7), or when myristoylated (16). Like the intact molecule, this CSD peptide binds to PKC and ERK and inhibits their activity (13,16,22). The CSD peptide is particularly useful because it is functional when delivered in vivo (7,29). Thus, disclosed herein are methods of treating fibrosis, wherein the CSD moiety comprises the sequence set forth in SEQ ID NO:1.

It is understood and herein contemplated that there are a number of variations of the CSD that can be used in the disclosed methods of treatment. Specifically contemplated herein are modifications or mutations made to the CSD that do not inhibit target binding (i.e., the ability to bind CBD), but can aid the CSD in, for example, avoiding proteolysis. Thus, in one aspect, the CSD can be a peptide as set forth in SEQ ID NO:1. It is understood and herein contemplated that modifications to the peptide R groups can affect the stability of the peptide. Therefore, specifically contemplated are modifications to the peptide backbone that add to the CSD moiety.

It is further understood that administering a peptide to the inside of a cell can be difficult. Therefore, specifically contemplated herein are any known modifications that can be made to the caveolin-1 or CSD moiety that can aid entry into a cell. For example, the Antennapedia internalization sequence can aid in the ability to cross the plasma membrane. Thus, contemplated herein are methods of treating fibrosis comprising administering to a subject a CSD moiety wherein the CSD moiety is a fusion peptide comprising the caveolin-1 scaffolding domain and the C-terminus of the Antennapedia internalization sequence. Thus, in one aspect disclosed herein are fusion proteins comprising a CSD moiety and the Antennapedia internalization sequence as set forth in SEQ ID NO:3. Thus, in another aspect, disclosed herein are methods of treatment wherein the CSD moiety comprises a fusion of the peptide set forth in SEQ ID NO:1 and SEQ ID NO:1. Also contemplated herein are modifications such as myristoylation. Therefore, disclosed herein are methods of treating fibrosis in a subject comprising administering to the subject a CSD moiety wherein the CSD moiety is myristolated. Also disclosed herein are methods wherein the CSD moiety is a peptidomimetic or a peptoid.

2. Peptoids

Peptoids represent a novel class of easily-designed, easily synthesized, potential peptidomimetic agents. Peptoids are oligo(N-alkyl) glycines that differ from peptides in that side chains are connected to the amide nitrogens rather than to the a carbon atoms. In many cases, peptoids synthesized with side chains equivalent to those in a peptide of interest retain the activity of the peptide of interest. Therefore, disclosed herein are methods of treating fibrosis in a subject in need thereof comprising administering to the subject a composition comprising a caveolin-1 scaffolding domain (CSD) moiety or a fragment, derivative, or analogue thereof, wherein the CSD moiety is a peptoid.

It is understood and herein contemplated that CSD treat fibrosis through the binding to calveolin-1 binding domains. It is further understood that any variant of CSD such as fragments, derivatives or analogues of CSD or agent capable of binding to a calveolin-1 binding domains (CBD) is also effective in the treatment of fibrosis. The identity of such agents or fragments, analogues, or derivatives of CSD can be determined by the ability to bind CBD. Thus, for example, disclosed herein are methods of treating fibrosis in a subject in need thereof comprising administering to the subject an agent that binds CBD.

It is contemplated herein that CBD include but are not limited to any peptide comprising the binding motif $\Phi X \Phi XXXX\Phi XX\Phi$ where $\Phi$ stands for any of the aromatic amino acids (F, W, or Y) and X stands for any amino acid. It is further understood that CBD can comprise any of the peptides as set forth in SEQ ID NOS: 4-19. Therefore, where a gent, CSD or fragment, analogue or derivative of CSD can bind to one or more of the peptides as set forth in SEQ ID NOS: 4-19, those a gents, CSDs or fragments, analogues or derivatives of CSD can be used to treat fibrosis. Therefore, disclosed herein are methods of treating fibrosis in a subject in need thereof comprising administering to the subject an agent that binds one or more peptides as set forth in SEQ ID NOS: 4-19.

It is understood and herein contemplated that the disclosed methods of treating fibrosis can be combined with any other method of treating fibrosis known in the art. Therefore, disclosed herein are methods of treating fibrosis in a subject in need thereof comprising administering to the subject a composition comprising a caveolin-1 scaffolding domain (CSD) moiety or a fragment, derivative, or analogue thereof, further comprising administering to the subject curcumin. Also disclosed are methods of treating fibrosis in a subject in need thereof comprising administering to the subject an agent that binds one or more peptides as set forth in SEQ ID NOS: 4-19, further comprising administering to the subject curcumin.

It is understood and herein contemplated that the disclosed methods of treating fibrosis can treat any fibrotic condition regardless of whether the fibrosis is the result of disease, accidental exposure to radiation, accidental tissue injury, therapeutic exposure to radiation, or surgical procedures. Thus, it is understood and herein contemplated that the disclosed methods can be used to treat fibrosis wherein the cause of the fibrosis includes but is not limited to pulmonary fibrosis caused by scleroderma lung disease, idiopathic pulmonary fibrosis (IPF), Bronchiolitis Olibterans Organizing Pneumonia (BOOP), Acute Respiratory Distress Syndrome (ARDS), asbestosis, accidental radiation induced lung fibrosis, therapeutic radiation induced lung fibrosis, Rheumatoid Arthritis, Sarcoidosis, Silicosis, Tuberculosis, Hermansky Pudlak Syndrome, Bagassosis, Systemic Lupus Erythematosis, Eosinophilic granuloma, Wegener's granulomatosis, Lymphangioleiomyomatosis, Cystic Fibrosis, Nitiofurantoin exposure, Amiodarone exposure, Bleomycin exposure, cyclophosphamide exposure, or methotrexate exposure as well as myocardial infarction, injury related tissue scarring, scarring form surgery, or therapeutic radiation induced fibrosis. Thus, for example, fibrosis in the throat following radiation treatment for throat cancer can be treated with the disclosed methods.

C. Methods Of Screening

Caveolin-1 or CSD binding to its ligand is known to have an inhibitory effect on fibrosis. It is understood and herein contemplated that the inhibitory effect can be the result of signaling through the ligands binding domain or the preventing of further signaling through the ligand. It is further contemplated herein that agents capable of binding the same binding site would have similar effect. For example, an agent that binds one or more of the peptides set forth in SEQ ID NOS: 4-19 can inhibit or treat fibrosis.

1. CSD Peptide and CBD Peptides

The ability of caveolin-1 to bind to a variety of kinases and thereby inhibit their activity has been mapped to a sequence known as the caveolin-1 scaffolding domain (CSD, amino acids 82-101 of caveolin-1) (23). A peptide equivalent to the CSD can cross the plasma membrane when synthesized as a fusion peptide on the C terminus of the Antennapedia internalization sequence (7) or when myristoylated (16). Like the intact molecule, this CSD peptide binds to PKC and ERK and inhibits their activity (22, 13, 16). The CSD peptide is particularly useful because it is functional when delivered in vivo (7, 29).

The sequence $\Phi X\Phi XXXX\Phi XX\Phi$ where $\Phi$ stands for any of the aromatic amino acids (F, W, or Y) and X stands for any amino acid was defined as a consensus ligand for the CSD peptide in a phage display experiment (57). Moreover, all or part of this caveolin-1-binding domain (CBD) sequence is present in almost every protein known to interact with caveolin-1 (23, 57). The ability of CBD peptides to interfere with the binding of the CSD peptide to ligands has been demonstrated both in biochemical, pull-down assays (9) and in cells in which the peptide was introduced by electroporation (58). The cell experiment was particularly noteworthy because the CBD peptide, in addition to inhibiting the binding of caveolin-1 to ligands, blocks the ability of caveolin-1 to act as a kinase inhibitor, thereby resulting in the hyperphosphorylation of multiple downstream kinases.

Thus, disclosed herein are methods of screening for agents that can treat fibrosis comprising contacting an agent with one or more of the peptides set forth in SEQ ID NOS: 4-19, wherein an agent that binds to the peptides indicates an agent that can treat fibrosis. It is understood and herein contemplated that the agent can comprise any molecule that will by one or more of the disclosed peptides set forth in SEQ ID NOS: 4-19. Thus, for example, the agent can be a peptide that binds the CBD of SEQ ID NO: 4, SEQ ID NO: 5, SEQ ID NO: 6, SEQ ID NO: 7, SEQ ID NO: 8, or SEQ ID NO: 9. It is understood and herein contemplated that one means for screening for the above agents is to determine if the agent can competitively inhibit the binding of a molecule that is known to bind the disclosed peptides. For example, an agent that competitively inhibits the binding of caveolin-1 or CSD with one or more of the peptides disclosed herein. Thus, disclosed herein are methods of screening, further comprising contacting caveolin-1 or CSD with one or more of the peptides set forth in SEQ ID NOS: 4-19 concurrently with the agent, wherein an agent that can competitively inhibit the binding of caveolin-1 or CSD and the peptides is an agent that can treat fibrosis.

D. Methods Of Identifying Targets

Disclosed herein are methods of identifying targets for the treatment of fibrosis comprising contacting CSD or caveolin-1 with a molecule wherein the ability of CSD to bind the molecule indicates the molecule is a target for the treatment of fibrosis. It is understood and herein contemplated that there are limited structures to which a particular peptide or protein can bind. Therefore, the ability of the calveolin-1 of CSD to bind a molecule indicates that the bound molecule is likely to be similarly effected by calveolin-1 or CSD as CBD and therefore a target for agents in the treatment of fibrosis.

E. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular caveolin-1, caveolin-1-binding domain, or caveolin-1 scaffolding domain is disclosed and discussed and a number of modifications that can be made to a number of molecules including the caveolin-1, caveolin-1-binding domain, or caveolin-1 scaffolding domain are discussed, specifically contemplated is each and every combination and permutation of caveolin-1, caveolin-1-binding domain, or caveolin-1 scaffolding domain and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. The peptides, and related molecules disclosed herein can be used as targets for the combinatorial approaches. Also disclosed are the compositions that are identified through combinatorial techniques or screening techniques in which the compositions disclosed in SEQ ID NOS: 4-19 or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, CBD, are also disclosed. Thus, the products produced using the combinatorial or screening approaches that involve the disclosed compositions, such as, CBD and CSD, are also considered herein disclosed.

It is understood that the disclosed methods for identifying molecules that competitively inhibit interactions between, for example, calveolin-1 and CBD can be performed using high through put means. For example, putative inhibitors can be identified using Fluorescence Resonance Energy Transfer (FRET) to quickly identify interactions. The underlying theory of the techniques is that when two molecules are close in space, i.e., interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, TIBS 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. *Proc. Natl. Acad. Sci. USA,* 94(23) 12997-302 (1997)).

Another preferred method for combinatorial methods designed to isolate peptides is described in Cohen et al. (Cohen B. A., et al., *Proc. Natl. Acad. Sci. USA* 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae,* is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxyamino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

b) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The peptides and related molecules disclosed herein, for example, CSB and CBD (e.g., SEQ ID NOS: 4-19) can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as, caveolin-1, CBD, and CSD (including the variants of CBD disclosed in SEQ ID NOS: 4-19), are also disclosed. Thus, the products produced using the molecular modeling approaches that involve the disclosed compositions, such as, caveolin-1, CBD, and CSD (including the variants of CBD disclosed in SEQ ID NOS: 4-19), are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

2. Compositions with Similar Functions

It is understood that the compositions disclosed herein have certain functions, such as inhibiting fibrosis or binding caveolin binding domain. Disclosed herein are certain structural requirements for performing the disclosed functions, and it is understood that there are a variety of structures which can perform the same function which are related to the disclosed structures, and that these structures will ultimately achieve the same result, for example inhibition of fibrosis or collagen production.

3. Homology/Identity

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. It is understood that one way to define any known variants and derivatives or those that might arise, of the disclosed genes and proteins herein is through defining the variants and derivatives in terms of homology to specific known sequences. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

4. Peptides a) Protein Variants

As discussed herein there are numerous variants of the caveolin-1 protein and caveolin-1 binding domain peptides and caveolin-1 scaffolding domain peptide that are known and herein contemplated. In addition, to the known functional caveolin-1, caveolin-1-binding domain, or caveolin-1 scaffolding domain strain variants there are derivatives of the caveolin-1 proteins, caveolin-1-binding domain peptides, and caveolin-1 scaffolding domain peptides which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | AlaA |
| allosoleucine | AIle |
| arginine | ArgR |
| asparagine | AsnN |
| aspartic acid | AspD |
| cysteine | CysC |
| glutamic acid | GluE |
| glutamine | GlnK |
| glycine | GlyG |
| histidine | HisH |
| isolelucine | IleI |
| leucine | LeuL |
| lysine | LysK |
| phenylalanine | PheF |
| proline | ProP |
| pyroglutamic acidp | Glu |
| serine | SerS |
| threonine | ThrT |
| tyrosine | TyrY |
| tryptophan | TrpW |
| valine | ValV |

TABLE 2

Amino Acid Substitutions

Original Residue Exemplary Conservative
Substitutions, others are known in the art.

Ala ser
    Arg lys, gin
    Asn gln; his
    Asp glu
    Cys ser
    Gln asn, lys
    Glu asp
    Gly pro
    His asn; gln
    Ile leu; val
    Leu ile; val
    Lys arg; gln;
    Met Leu; ile
    Phe met; leu; tyr
    Ser thr
    Thr ser
    Trp tyr
    Tyr trp; phe
    Val ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of caveolin-1 scaffolding domain. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs.

These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology*, 3:348-354 (1992); Ibba, *Biotechnology & Genetic Engineering Reviews* 13:197-216 (1995), Cahill et al., *TIBS*, 14(10):400-403 (1989); Benner, *TIB Tech*, 12:158-163 (1994); Ibba and Hennecke, *Biotechnology*, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH—(cis and trans), —$COCH_2$—, —CH(OH) $CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., Vega Data (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) (—$CH_2NH$—, $CH_2CH_2$—); Spatola et al. *Life Sci* 38:1243-1249 (1986) (—$CHH_2$—S); Hann *J. Chem. Soc Perkin Trans.* 1307-1314 (1982) (—CH—CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—CH(OH)$CH_2$—); Holladay et al. *Tetrahedron. Lett* 24:4401-4404 (1983) (—C(OH)$CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

5. Nucleic Acids

There are a variety of molecules disclosed herein that are nucleic acid based, including for example the nucleic acids that encode, for example, caveolin-1, the caveolin-1-binding domain, or the caveolin-1 scaffolding domain as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, which the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989,86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to, for example, caveolin-1 binding domain and caveolin-1 scaffolding domain peptides as well as any other protein disclosed herein that are disclosed on Genbank, and these sequences and others are herein incorporated by reference in their entireties as well as for individual subsequences contained therein.

A variety of sequences are provided herein and these and others can be found in Genbank, at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

c) Primers and Probes

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the polypeptide CBD. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci. USA* 89:8006-8010 (1992); WO 93/22434 by Yale; WO 95/24489 by Yale; Yuan and Altman, *EMBO J.* 14:159-168 (1995), and Carrara et al., *Proc. Natl. Acad. Sci.* (*USA*) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

6. Delivery of the Compositions to Cells

There are a number of compositions and methods which can be used to deliver nucleic acids, peptides, or proteins to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physicomechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)).

As used herein, plasmid or viral vectors are agents that transport the disclosed nucleic acids, such as the nucleic acids that encode caveolin-1 or CSD into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In *Microbiology* 1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J Virology* 61:1213-1220 (1987); Massie et al., *Mol. Cell. Biol.* 6:2872-2883 (1986); Haj-Ahmad et al., *J Virology* 57:267-274 (1986); Davidson et al., *J Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-asscociated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature Genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable the maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed CSD-antennapedia internalization sequence fusions, myristolized CSD or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.,* 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.,* 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In vivo/ex vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

7. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell. Bio.* 3: 1108 (1983)) to the transcription unit. Furthermore, enhancers can be within an intron (Baneiji, J. L. et al., *Cell* 33: 729 (1983)) as well as within the coding sequence itself (Osborne, T. F., et al., *Mol. Cell. Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions (including but not limited to oil:water and water:oil:water emulsions). Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms/disorder are/is effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as a peptide or peptidomimetic, for treating, inhibiting, or preventing an fibrosis, the efficacy of the therapeutic peptide or peptidomimetic can be assessed in various ways well known to the skilled practitioner. For instance, one of ordinary skill in the art will understand that a composition, such as an peptide or peptidomimetic, disclosed herein is efficacious in treating or inhibiting an fibrosis in a subject by observing that the composition binds caveolin-1 binding domain or reduces fibrosis.

The compositions that inhibit fibrosis interactions disclosed herein may be administered prophylactically to patients or subjects who are at risk for fibrosis, for example, patients preparing to undergo radiation treatment for a cancer such as throat cancer, where fibrosis from radiation damage is a possibility.

The disclosed compositions and methods can also be used for example as tools to isolate and test new drug candidates for a variety of fibrosis related diseases including but not limited to, for example, scleroderma lung disease, idiopathic pulmonary fibrosis (IPF), Bronchiolitis Olibterans Organizing Pneumonia (BOOP), Acute Respiratory Distress Syndrome (ARDS), asbestosis, accidental radiation induced lung fibrosis, therapeutic radiation induced lung fibrosis, Rheumatoid Arthritis, Sarcoidosis, Silicosis, Tuberculosis, Hermansky Pudlak Syndrome, Bagassosis, Systemic Lupus Erythematosis, Eosinophilic granuloma, Wegener's granulomatosis, Lymphangioleiomyomatosis, Cystic Fibrosis, Nitiofurantoin exposure, Amiodarone exposure, Bleomycin exposure, cyclophosphamide exposure, methotrexate exposure, myocardial infarction, injury related tissue scarring, scarring form surgery, and therapeutic radiation induced fibrosis.

9. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

F. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

Interstitial lung disease (ILD) frequently complicates scleroderma (systemic sclerosis, SSc) and can be a debilitating disorder with a poor prognosis. SSc-ILD is now the leading causes of death in SSc (38) and there are few, if any, safe and effective treatment options (39). Lung tissue from SSc-ILD patients is fibrotic, containing abnormally high levels of collagen I (hereafter referred to as collagen) and other extracellular matrix (ECM) proteins such as tenascin-C. These ECM proteins are synthesized primarily by an activated population of α-smooth muscle actin (ASMA)-positive fibroblasts known as myofibroblasts. Normal human lung fibroblasts (NLF) and fibroblasts from the lung tissue of scleroderma patients (SLF) are useful for studying lung fibrosis because they retain their in vivo phenotypes, i.e. SLF overexpress collagen, tenascin-C, and ASMA (5,42), for at least four passages in vitro.

The progression of lung fibrosis in vivo can be studied in an animal model in which rodents receive intratracheal bleomycin. While intratracheal bleomycin is not a perfect model for human disease, it is a very convenient and reliable model and is the best available model for scleroderma lung disease and for idiopathic pulmonary fibrosis (IPF) (12,48). Bleomycin-induced fibrosis is similar to scleroderma and to IPF in that the disease can progress rapidly, the distribution of fibrosis within the tissue is patchy rather than diffuse, and proliferating fibroblasts overexpress collagen and tenascin-C and are ASMA-positive (53,54).

The goal in the current studies was to determine how the interplay between caveolin-1 and several other signaling molecules (MEK, ERK, JNK, PI3K, Akt, and PI3K [phosphoinositide-3 kinase]) regulates the expression of collagen, tenascin-C, and ASMA in NLF and SLF in vitro and the progression of lung fibrosis in vivo. The CSD peptide was chosen rather than adenovirus as the primary method of up-regulating caveolin-1 function because the results of such studies can to lead to novel treatments that can be used in human patients, and because the practical and regulatory hurdles to using virus to up-regulate caveolin-1 in humans are significant. Major results of the studies include: Although caveolin-1 inhibits the activation of MEK, ERK, JNK, and Akt in both NLF and SLF and inhibits the expression of collagen, tenascin-C, and ASMA, details of the signaling cascades involving these molecules differ between NLF and SLF; studies on the expression of signaling molecules in fibrotic lung tissue from human patients and bleomycin-treated mice validate the relevance of the bleomycin model to human disease; and treatment with the CSD peptide blocks both changes in tissue morphology and changes in signaling molecule expression associated with lung fibrosis. In summary, the results strongly indicate that the CSD peptide inhibits collagen, tenascin-C, and ASMA expression in vitro and the progression of lung fibrosis in vivo through similar molecular mechanisms. A portion of this work has been presented previously in abstracts (45, 46).

a) Materials and Methods (1) Cell Culture.

Fibroblasts were derived from lung tissue obtained at autopsy from scleroderma patients (SLF) and from age-, race-, and sex-matched normal subjects (NLF) and cultured as previously described (44). Cells were used in passages 2-4. The group of scleroderma patients fulfilled the criteria of American college of Rheumatology for the diagnosis of scleroderma with lung involvement. Normal human lung tissue was obtained from the Brain and Tissue Bank for Developmental Disorders (Baltimore, Md.) or from the National Disease Research Interchange (Philadelphia, Pa.). Scleroderma lung tissue was obtained from the Division of Pathology and Laboratory Medicine at the Medical University of South Carolina (MUSC). The study was approved by the Institutional Review Board for Human Subject Research at the MUSC.

(2) Perturbation of Caveolin-1 Expression.

(a) CSD Peptide

The CSD peptide (amino acids 82-101 of caveolin-1; DGIWKASFTTFTVTKYWFYR) (SEQ ID NO: 1) and a scrambled control peptide (WGIDKAFFTTSTVTKWFRY) (SEQ ID NO: 2) were synthesized as fusion peptides to the C terminus of the *Antennapedia* internalization sequence (RQIKUVFQNRRMKWKK) (SEQ ID NO: 3). Before each experiment, desiccated peptides were dissolved at a final 1 mM in 10% DMSO as described by Bernatchez et al. (4). Cells in 6-well plates at 70-80% confluence were then incubated with 1 ml serum-free DMEM containing 51M CSD or scrambled peptide. After 6 h, the culture medium and cell layer were harvested.

(b) Adenovirus

Recombinant adenovirus containing myc-tagged caveolin-1 and control, empty adenovirus (37) were a generous gift from Dr. William Sessa (Yale University School of Medicine, New Haven, Conn.). Amplification, titering, and infection were performed as described by Pannu et al. (24). After 48 h the medium was replaced with fresh serum-free medium. After an additional 6 h, cells and medium were harvested.

(c) siRNA siRNA was used to knock down caveolin-1 expression as previously described (44).

(3) Kinase Inhibitors.

U0126 (MEK inhibitor), SP600125 (JNK inhibitor), LY294002 (PI3 kinase inhibitor) and Akt inhibitor VIII were purchased from Calbiochem and dissolved in DMSO (mM). Cells in 6-well plates were treated with 10 μM of inhibitors in serum-free medium for 6 h (U0126) or 24 h for the other inhibitors prior to the harvesting of cells and medium.

(4) Western Blot Analyses.

Cell layers were harvested in boiling SDS-PAGE sample buffer; medium was dialyzed, lyophilized, and resuspended in sample buffer. Aliquots of culture medium or of cell layer representing material derived from the same number of cells was probed using the following primary antibodies and appropriate secondary antibodies. Culture medium: goat anti-human collagen I (AB758P) and rabbit anti-human tenascin-C (AB19011) from Chemicon International (Temecula, Calif.). Cell layer: rabbit antibodies against PKCα (sc-208), PKCε (sc-214), activated JNK (sc-12882), activated Akt Thr 308 (sc-166646R) and caveolin-1 (sc-894) from Santa Cruz Biotechnology (Santa Cruz, Calif.); rabbit antibodies against ERK 1/2 (9102), activated ERK 1/2 (9106), JNK (9252), Akt (9272), MEK 1/2 (9122), and activated MEK 1/2 (9121) from Cell Signaling (Beverly, Mass.); mouse monoclonal anti-ASMA (clone 1A4) from Sigma (Saint Louis, Mo.), and mouse monoclonal anti-actin (MAB1501) from Chemicon International (Temecula, Calif.).

(5) Immunocytochemistry and Laser Confocal Microscopy.

NLF and SLF were cultured in 4-well glass chamber slides (Nalge Nunc International, Naperville, Ill.) and stained as previously described (43) using the indicated primary antibodies and appropriate secondary antibodies tagged with Alexa Fluoro® 488 (Molecular Probes, Eugene, Oreg.). Nuclei were stained with 7-aminoactinomycin D (Molecular Probes, Eugene, Oreg.). Images were acquired using a Zeiss 510SML Laser Confocal Microscope (excitation S490/20, emission D528/38) fitted with an oil-immersion objective (40×/1.4).

(6) Bleomycin-Induced Lung Fibrosis and CSD Treatment.

This procedure was approved by the MUSC Institutional Animal Care & Use Committee. Ten-week old, male CD 1 mice (Charles River, Boston, Mass.) were anesthetized and received bleomycin (Calbiochem, La Jolla, Calif.) or saline solution by intratracheal instillation as previously described (44). Two approaches were used for CSD peptide treatment. In both approaches the peptide treatment was initiated one day prior to bleomycin. In the first approach, Alzet pumps delivering 0.5 μl/h for 14 days of a 1 mM solution of CSD peptide were implanted into twelve mice; twelve additional mice received no pump. In the second approach twelve mice received daily intraperitoneal injections of 100 μl of a 0.15 mM solution of the CSD peptide for 14 days; twelve additional mice received the scrambled peptide. One day later, six mice from each group of twelve received intratracheal bleomycin, six received saline. After 14 days, lungs were harvested. Half of each set of lungs was fixed, sectioned, and stained with Masson's Trichrome Stain. The other half of each set of lungs was dissolved in SDS-PAGE sample buffer for Western blotting experiments. Because very similar results were obtained using the two approaches to CSD peptide treatment, results were pooled.

(7) Statistical Analysis.

Immunoreactive bands were quantified by densitometry using the Image 1.32J NIH software. For statistical analysis the raw densitometric data were processed and analyzed using the Prism 3.0 (GraphPad Software Inc.) statistical analysis software.

Student's t test was used to analyze protein expression levels in lung tissue samples obtained from normal individuals and from scleroderma patients. Protein expression levels for samples obtained from in vitro experiments and from mice were analyzed by two-way analysis of variance (ANOVA) followed by the Bonferroni post-test. For experiments in which the degree of tissue damage in mice treated with bleomycin was scored on an arbitrary scale, data was analyzed using the Mann-Whitney rank sum test. In all tests, results were regarded as statistically significant if $p<0.05$.

b) Results

Caveolin-1 depletion upregulates collagen expression in lung fibroblasts via a mechanism involving the activation of MEK and ERK (44). Herein demonstrated that collagen expression is inhibited when cells are treated with a membrane-permeable peptide from the scaffolding domain of caveolin-1 (CSD peptide) that is known to mimic the kinase-inhibiting activity of full-length caveolin-1 (13,16,22). Also demonstrated herein is that caveolin-1 also regulates the expression of the myofibroblast differentiation marker ASMA and of the ECM protein tenascin-C. Also shown herein is that extending the signaling cascade that regulates the expression of collagen, tenascin-C, and ASMA to include JNK, Akt, and PI-3 kinase; 4) validating the relevance of this signaling cascade to the progression of lung fibrosis in vivo; and 5) demonstrating that CSD peptide treatment blocks the progression of bleomycin-induced lung fibrosis in vivo.

(1) CSD Peptide Inhibits Collagen Expression by Lung Fibroblasts.

Throughout these studies, collagen expression in cultured lung fibroblasts was quantified in terms of its accumulation in the culture medium. When collagen expression by normal lung fibroblasts (NLF) or scleroderma lung fibroblasts (SLF) treated with CSD peptide or with the control, scrambled peptide (Scr) was compared, the CSD peptide was found to inhibit collagen expression by >95% (FIG. 1). This effect was rapid, occurring in less than 5 hours, and powerful, occurring at 5 µM CSD. The CSD peptide decreased MEK/ERK activation by about 50%. In contrast, the CSD peptide did not affect the expression of caveolin-1 itself, PKCα, or PKCε.

To provide additional confirmation for the link between caveolin-1, ERK activation, and collagen expression in lung fibroblasts, NLF and SLF were infected with adenovirus encoding caveolin-1 or with control virus lacking a cDNA insert. FIG. 2A demonstrates that infecting cells with adenovirus encoding caveolin-1 results in partial inhibition of ERK activation and almost complete inhibition of collagen expression. As with CSD peptide treatment, this treatment did not affect the expression of PKCα or PKCε. FIG. 2B demonstrates the dose-dependence of treatment with adenovirus encoding caveolin-1 on collagen expression. Thus, each of two very different treatments that increase caveolin-1 expression in cells results in the partial inhibition of ERK activation and in the almost complete inhibition of collagen expression.

(2) Caveolin-1 Regulates the Expression of ASMA and Tenascin-C.

Because myofibroblasts overexpress collagen (44), the regulation of caveolin-1 on myofibroblast differentiation was evaluated in addition to regulating collagen expression. Therefore, the effects of up- and down-regulating caveolin-1 expression on the expression of the myofibroblast differentiation marker ASMA in NLF (i.e. fibroblasts) and SLF (a myofibroblast-rich population expressing ASMA at high levels) was determined. Striking differences were observed between NLF and SLF. siRNA-mediated inhibition of caveolin-1 expression increased ASMA expression in NLF, but not in SLF (FIG. 3AB). Conversely, overexpression of caveolin-1 mediated by the CSD peptide (FIG. 3CD), or by adenovirus (FIG. 2), inhibited ASMA expression in SLF, but not in NLF. In summary, decreasing caveolin-1 expression increases ASMA expression in cells expressing relatively low levels of ASMA but not in cells already expressing high levels of ASMA; increasing caveolin-1 expression decreases ASMA expression in cells expressing high levels of ASMA but not in cells expressing relatively low levels of ASMA.

In addition to overexpressing collagen, myofibroblasts also overexpress tenascin-C (42). Therefore, to determine whether caveolin-1 regulates both the differentiation and function of myofibroblasts, the effect on tenascin-C expression of perturbing caveolin-1 expression was evaluated. siRNA-mediated inhibition of caveolin-1 expression increased tenascin-C expression in NLF, but not in SLF, just as it increased ASMA expression (FIG. 3) and collagen expression in NLF but not SLF (44). Caveolin-1 overexpression mediated by the CSD peptide (FIG. 3) or by adenovirus (FIG. 2) inhibited tenascin-C expression in both SLF and NLF, just as it inhibited collagen expression (FIG. 1). In contrast, the CSD peptide inhibited ASMA expression in SLF but not NLF (FIG. 3CD). The combined observations support the idea that the decreased level of caveolin-1 present in SLF regulates both their differentiation into myofibroblasts and their overexpression of ECM proteins.

(3) Tenascin-C Expression is MEK/ERK Dependent, ASMA Expression is MEK/ERK Independent.

Collagen expression is regulated by MEK/ERK signaling in both NLF and SLF (44). To determine whether the expression of tenascin-C and ASMA are also regulated by MEK/ERK, cells were treated with the MEK inhibitor U0126. While U0126 inhibited tenascin-C expression in both NLF and SLF, ASMA expression was unaffected by U0126 in both cell types (FIG. 4). Thus, the signaling cascade through which caveolin-1 regulates collagen and tenascin-C expression appears to include MEK/ERK, while the cascade through which caveolin-1 regulates ASMA expression must include different intermediates.

(4) Signaling Cascades Regulating the Expression of Collagen, Tenascin-C, and ASMA.

In order to identify the distinct signaling cascades that regulate the expression of collagen, tenascin-C, and ASMA in normal and fibrotic lung tissue, the levels of activated MEK, ERK, Akt, and JNK were evaluated in NLF and SLF treated with the CSD peptide or the Scr peptide. The activation of MEK and ERK is upregulated in SLF as compared to NLF (44). Herein is shown that the activation of Akt and JNK, in accord with Shi-Wen et al. (35) is also upregulated in SLF (FIG. 5). Consistent with the ability of caveolin-1 to inhibit the activation of a variety of kinases, in both NLF and SLF treatment with the CSD peptide inhibited the activation of Akt and JNK (FIG. 5) in addition to MEK and ERK (FIG. 1). In contrast, the CSD peptide did not affect the expression of total MEK, total ERK, total Akt, or total JNK.

To further elucidate cross-talk between MEK/ERK, Akt, PI3K, and JNK, and the ability of these kinases to regulate the expression of collagen, tenascin-C, and ASMA, NLF and SLF were treated with the MEK inhibitor U0126, the JNK inhibitor SP600125, Akt inhibitor VIII, and the PI3K inhibitor LY294002. While U0126 blocked ERK activation and collagen and tenascin-C expression as described above (FIG. 4), it had little or no effect on the activation of JNK and Akt (FIG. 6a), or on the expression of ASMA (FIG. 4).

SP600125 inhibited the activation of JNK, ERK, and Akt in both NLF and SLF (FIG. 6b). The inhibition of JNK activation by SP600125 raises the possibility that the form of JNK present in these cells is JNK2, which is known to undergo autophosphorylation (10). SP600125 also had a consistent inhibitory effect on collagen and tenascin-C expression in both NLF and SLF; however, it inhibited ASMA expression in SLF yet had no effect on ASMA expression in NLF (FIG. 6b).

Akt inhibitor VIII inhibited the activation of Akt and enhanced the activation of ERK in both NLF and SLF (FIG. 6c). This inhibition of Akt activation is consistent with its known autophosphorylation (41). While Akt inhibitor VIII had no effect on JNK activation in NLF, it enhanced JNK activation in SLF. Akt inhibitor VIII inhibited collagen and tenascin-C expression and had no effect on ASMA expression in NLF (FIG. 6c). Conversely, Akt inhibitor VIII inhibited ASMA expression and had no effect on collagen and tenascin-C expression in SLF (FIG. 6c).

LY294002 inhibited Akt activation, enhanced ERK activation, and had no effect on JNK activation in both NLF and SLF (FIG. 6c). These observations are consistent with the fact that PI3K is frequently placed immediately upstream from Akt in signaling cascades. Like Akt inhibitor VIII, LY294002 inhibited collagen and tenascin-C expression in NLF, had no effect on ASMA expression in NLF, and inhibited ASMA expression in SLF (FIG. 6c). However, LY294002 inhibited collagen and tenascin-C expression in SLF, even though Akt inhibitor VIII had no effect on these cells (FIG. 6c). These observations indicate that in SLF, PI3K regulates collagen and tenascin-C expression via an Akt-independent mechanism. The results of these experiments are summarized in Table 1. A model summarizing all the data on the regulation of collagen, ASMA, and tenascin-C expression by signaling cascades involving caveolin-1, MEK/ERK, JNK, PI3K, and Akt is presented in the FIG. 14.

TABLE 1

Effects of Signaling Inhibitors on Various Targets

| Target | Inhibitor | | | | | | | |
|---|---|---|---|---|---|---|---|---|
| | MEK | | JNK | | Akt | | PI3K | |
| | NLF | SLF | NLF | SLF | NLF | SLF | NLF | SLF/ |
| Ph-ERK | ↓ | ↓ | ↓ | ↓ | ↑ | ↑ | ↑ | ↑ |
| Ph-JNK | — | — | ↓ | ↓ | — | ↑ | — | — |
| Ph-Akt | — | — | ↓ | ↓ | ↓ | ↓ | ↓ | ↓ |
| Collagen | ↓ | ↓ | ↓ | ↓ | ↓ | — | ↓ | ↓ |

TABLE 1-continued

Effects of Signaling Inhibitors on Various Targets

| Target | Inhibitor | | | | | | | |
|---|---|---|---|---|---|---|---|---|
| | MEK | | JNK | | Akt | | PI3K | |
| | NLF | SLF | NLF | SLF | NLF | SLF | NLF | SLF/ |
| Tenascin-C | ↓ | ↓ | ↓ | ↓ | ↓ | — | ↓ | ↓ |
| ASMA | — | — | — | ↓ | — | ↓ | — | ↓ |

NLF and SLF in serum-free medium were treated with inhibitors (10 µM) of the indicated kinases (MEK, U0126; JNK, SP600125; Akt, Akt inhibitor VII; PI3K, LY294002). Levels of collagen and tenascin-C in the medium and ph-ERK, ph-JNK, ph-Akt, and ASMA in the cell layer were detected by Western blotting and quantified densitometrically. No changes in actin (loading control) were observed. The observed changes in protein expression are summarized here as a decrease ↓, an increase ↑, or no effect —. Similar results were obtained with three pairs of NLF and SLF. All of the decreases and increases indicated here were statistically significant at $p < 0.01$.

(5) Immunohistochemical (IHC) Detection of Signaling Molecules.

In order to confirm and extend the results of the Western blotting experiments described above, the effects of the CSD peptide on the levels of expression and distribution of caveolin-1, activated ERK, activated JNK, and activated Akt were examined. The low level of caveolin-1 in SLF as compared to NLF (see FIG. 1 and ref. 44) was confirmed by IHC (FIG. 7). In both cell types treated with the control Scr peptide, caveolin-1 was detected primarily in a punctuate pattern in the cytoplasm. In accord with FIG. 1, the CSD peptide did not affect the level of caveolin-1 expression detected by IHC (FIG. 7). However, the distribution of caveolin-1 staining was altered in both cell types, with staining associated with the plasma membrane becoming more prominent, particularly in SLF.

The high level of activated ERK present in SLF as compared to NLF (see FIG. 1) was also confirmed by IHC (FIG. 7). While activated ERK in NLF treated with the control peptide is primarily localized in the nucleus and the perinuclear region, activated ERK in control SLF is present in the perinuclear region and in an intensely labeled punctuate pattern in the cytoplasm. As observed in FIG. 1, the CSD peptide decreases the level of activated ERK in both NLF and SLF (FIG. 7). This residual staining is primarily perinuclear and cytoplasmic in both NLF and SLF.

The high level of activated JNK present in SLF as compared to NLF (see FIG. 5) was also confirmed by IHC (FIG. 8). While activated JNK in NLF treated with the control peptide is primarily perinuclear, intense punctate cytoplasmic staining is observed in addition to perinuclear staining in SLF. As observed in FIG. 5, the CSD peptide decreases the level of activated JNK in both NLF and SLF (FIG. 8). In both cell types, this treatment preferentially decreased perinuclear staining and increased staining associated with the plasma membrane. In SLF, CSD peptide treatment also eliminated the intense punctate cytoplasmic staining observed in cells treated with the control peptide.

Finally, the high level of activated Akt present in SLF as compared to NLF (see FIG. 5) was also confirmed by IHC (FIG. 8). Both cell types exhibited nuclear and perinuclear staining; punctate cytoplasmic staining was also apparent in both cell types, but was particularly prominent in SLF. As observed in FIG. 5, the CSD peptide decreases the level of activated Akt in both NLF and SLF (FIG. 8). In both cell types, this treatment preferentially decreased perinuclear, nuclear, and cytoplasmic staining while increasing staining associated with the plasma membrane.

In summary, the IHC studies in FIGS. 7 and 8 confirmed the results of the Western blotting experiments in FIGS. 1 and 5 regarding the relative levels of caveolin-1, activated ERK, activated JNK, and activated Akt in NLF and SLF, as well as the effects of the CSD peptide on these levels. In addition, FIGS. 7 and 8 revealed differences in the distribution patterns of these signaling molecules in NLF and SLF and cell-type specific differences in the effect of the CSD peptide on these distribution patterns. These observations raise the possibility that the CSD peptide alters the trafficking of these signaling molecules between organelles and that the trafficking of these molecules is different in NLF and SLF.

(6) Signaling Molecule Expression in Normal and Fibrotic Human Lung Tissue In vivo.

Caveolin-1, PKCε, ph-MEK, and ph-ERK were involved in the regulation of collagen expression in NLF and that their expression was altered in SLF, leading to the over-expression of collagen by these cells (44). Herein is demonstrated that ph-JNK and ph-Akt are also involved in the regulation of collagen expression in NLF and that their expression is altered in SLF. To evaluate whether similar alterations could be detected in the expression of these signaling molecules in vivo, the levels of these proteins in autopsy specimens of normal lung tissue and of fibrotic lung tissue from scleroderma patients were examined. Extremely consistent results were obtained in a Western blotting experiment using three samples from each source (FIGS. 9A, B). In particular, in accord with results obtained with NLF and SLF, caveolin-1 and PKCε levels were very low in lung tissue from scleroderma patients while ph-MEK, ph-ERK, ph-JNK, and ph-Akt were present at very high levels. The levels of actin (loading control) and of total ERK, JNK, and Akt were similar in normal and scleroderma lung tissue (FIGS. 9A, B). While total MEK was present at elevated levels in scleroderma lung tissue (2.5-fold increase), this elevation was still much less than for ph-MEK (6.5-fold increase). In general, the changes in these signaling molecules associated with fibrosis in vivo were more extreme than the differences that were observed between NLF and SLF (44), indicating that while NLF and SLF retain the signaling properties of fibroblasts and myofibroblasts in vivo, these differences are attenuated during culture.

In the case of PKCα, much lower levels were observed in scleroderma lung tissue than in normal lung tissue (FIGS. 9A,B), even though no difference had been observed between NLF and SLF (44). This observation is consistent with the observation that PKCα regulates caveolin-1 expression (44).

In addition, the levels of caveolin-1, of the ECM proteins collagen and tenascin-C, and of the myofibroblast marker ASMA were compared in normal and scleroderma lung tissue by histochemistry and IHC (FIG. 10). In accord with the Western blotting data, there was much less caveolin-1 in scleroderma lung tissue than in normal lung tissue. As expected, collagen (detected using Masson's trichrome stain) was present at much higher levels in scleroderma lung tissue than in normal lung tissue (FIG. 10). While tenascin-C was present at higher levels in scleroderma lung tissue than in normal lung tissue by Western blot (FIGS. 9A, B), the difference was not statistically significant. Nevertheless, IHC data support the idea that tenascin-C is present at higher levels in scleroderma lung tissue than in normal lung tissue. Finally, while ASMA was also present at higher levels in scleroderma lung tissue than in normal lung tissue (FIGS. 9A, B), again the difference was not statistically significant. These limited differences in tenascin-C and ASMA expression are due to the relatively late stage of the disease in the available autopsy tissue, given that the highest levels of ASMA-positive myofibroblasts are present during the early, active stage of scleroderma lung disease (3). Examination of ASMA staining (FIG. 10) demonstrates that there is a striking increase in the number of ASMA-positive cells present in fibrotic scleroderma lung tissue, but that the loss of vascular smooth muscle and bronchiolar smooth muscle associated with fibrosis limits the level of the increase in ASMA that can be detected by Western blotting.

(7) Validation of the Bleomycin Model.

When bleomycin is administered to mice intratracheally, within two weeks 30-50% of the mice die. Those surviving show massive fibrosis with distortion of the alveoli and with filling of the tissue and the alveolar air space with various types of cells and with collagen and other ECM proteins. To verify the validity of bleomycin treatment of mice as a model system for human lung fibrosis, Western blotting was performed for a variety of signaling molecules in control (saline-treated) and fibrotic (bleomycin-treated) mouse lung tissue. The results obtained with bleomycin-induced lung fibrosis (FIG. 11) were strikingly similar to the results obtained with fibrotic human (SSc) lung tissue (FIG. 9). In particular, in both cases PKCα, PKCε, and caveolin-1 were down-regulated in fibrotic tissue whereas ph-ERK, ph-JNK, and ph-Akt were all up-regulated. In addition, the ECM protein tenascin-C and the myofibroblast marker ASMA were up-regulated to a greater extent during bleomycin-induced lung fibrosis (FIG. 11) than in fibrotic human lung tissue (FIG. 9). All of these changes in protein expression between saline- and bleomycin-treated mouse lung tissues were statistically significant at $p<0.01$. These results strongly indicate that the same molecular mechanisms that regulate lung fibrosis in human patients also regulate lung fibrosis in the bleomycin model.

(8) CSD Provides Protection Against Bleomycin-Induced Lung Fibrosis.

Having verified the importance of caveolin-1 and other associated signaling molecules in the progression of lung fibrosis in vivo, the possibility that administration of the CSD peptide provides protection against bleomycin-induced fibrosis was tested. The results of these experiments were strikingly positive. Whereas bleomycin-treated mice that did not receive peptide routinely died or showed severe tissue damage and collagen deposition, bleomycin-treated mice that received peptide routinely showed only slight to moderate tissue damage and collagen deposition (FIG. 12). In addition, median weight loss improved from 30% of original weight in untreated mice to 14% in mice receiving peptide. Changes in the expression of signaling molecules, ASMA, and tenascin-C usually associated with bleomycin treatment were also inhibited by the peptide (FIG. 11). In particular, the increases in ph-ERK, ph-Akt, ph-JNK, ASMA, and tenascin-C and the decrease in PKCε were all inhibited by at least 75% and the decrease in PKCα was inhibited by about 50%. The CSD peptide did not affect the expression of caveolin-1 itself, strongly indicating that the CSD peptide alters the expression of proteins that are downstream from caveolin-1 in signaling cascades. Each of the observations reported here was highly reproducible and statistically significant ($p<0.02$). These observations on the lack of effect of CSD peptide treatment on caveolin-1 expression and on the effect of CSD peptide treatment on ASMA and tenascin-C expression were confirmed by IHC (FIG. 13). In summary, treatment with the CSD peptide provides a remarkable degree of protection against bleomycin-induced lung fibrosis.

c) Discussion

The results of the in vitro experiments support the model shown in FIG. 14 depicting the signaling cascades that regulate the expression of collagen, tenascin-C, and ASMA in NLF and SLF. The activation of MEK/ERK increases collagen expression and that knocking down caveolin-1 expression using siRNA increases MEK/ERK activation, again leading to increased collagen expression. Conversely, disclosed herein, up-regulating caveolin-1 function using either the CSD peptide (FIG. 1) or adenovirus (FIG. 2) inhibits MEK/ERK activation and collagen expression in both NLF and SLF. While up-regulating caveolin-1 function also inhibits tenascin-C expression in NLF and SLF, up-regulating caveolin-1 function inhibits ASMA expression only in SLF (FIGS. 2,3). Given that the MEK inhibitor U0126 inhibits ERK activation and the expression of collagen and tenascin-C, but has no effect on ASMA expression (FIG. 4), these results demonstrate that caveolin-1 regulates ASMA expression in SLF via a mechanism not involving MEK/ERK.

To identify signaling molecules involved in the regulation of ASMA expression by caveolin-1, the studies were extended to include JNK, PI3K, and Akt. Like activated MEK and ERK (FIG. 1), activated Akt and JNK are present at higher levels in SLF than in NLF, and their activation is inhibited by the CSD peptide (FIG. 5). Interestingly, the CSD peptide also altered the subcellular localization of caveolin-1 and activated ERK, JNK, and Akt (FIGS. 7, 8). Although the MEK inhibitor U0126 did not affect ASMA expression in either cell type, the JNK inhibitor SP600125, Akt inhibitor VIII, and the PI3K inhibitor LY294002 all inhibited ASMA expression in SLF, but not NLF (FIG. 6). Because the JNK inhibitor and the PI3K inhibitor each block the activation of Akt (FIG. 6), Akt is shown as being downstream from JNK and PI3K (FIG. 14). In turn, in the simplest scenario combining these observations (FIG. 14), ASMA is downstream from Akt.

Inhibitor studies (FIG. 6) provided additional information regarding the regulation of collagen and tenascin-C expression and the interplay between signaling molecules. The JNK inhibitor inhibited the activation of ERK and Akt in NLF and SLF. Therefore, JNK was placed upstream of ERK and Akt in FIG. 14. The Akt inhibitor promoted ERK activation in both NLF and SLF, but promoted JNK activation only in SLF. Therefore, Akt was placed as a negative upstream regulator of ERK in both NLF and SLF and of JNK only in SLF. PI3K and Akt are circled together because Akt is frequently, but not always, immediately downstream from PI3K in signaling cascades. The PI3K inhibitor promoted ERK activation, presumably by inhibiting Akt activation, thus leading to ERK activation (FIG. 14). Given that the Akt inhibitor inhibited collagen and tenascin-C expression in NLF but not SLF and that the PI3K inhibitor inhibited collagen and tenascin-C expression in both NLF and SLF, PI3K regulates collagen and tenascin-C expression via an Akt-independent mechanism in SLF (and possibly NLF), whereas PI3K also regulates collagen and tenascin-C expression via an Akt-dependent mechanism in NLF, but not SLF.

In vivo experiments demonstrate that the same signaling cascades that regulate the expression of collagen, tenascin-C, and ASMA in NLF and SLF also regulate their expression during the progression of a murine model of lung fibrosis. Collagen, tenascin-C, and ASMA expression are up-regulated in SLF and in the fibrotic lung tissue of SSc-ILD patients and bleomycin-treated mice (FIG. 9-12). Similarly, caveolin-1 and PKCε are down-regulated and activated MEK, ERK, JNK, and Akt are up-regulated in SLF, the fibrotic lung tissue of SSc-ILD patients, and bleomycin-treated mice (FIGS. 1,9,11). In addition, PKCα is down-regulated in the fibrotic lung tissue of SSc-ILD patients and bleomycin-treated mice (FIGS. 9,11), although its expression is similar in NLF and SLF (FIG. 1). These observations validate the relevance of both SLF as an in vitro model and bleomycin-treated mice as an in vivo model for the fibrosis observed in SSc-ILD.

Because the CSD peptide inhibits collagen, tenascin-C, and ASMA expression in vitro, this peptide also inhibits the progression of lung fibrosis in vivo. Indeed, systemic treatment with the peptide had a striking positive effect on the survival and lung tissue morphology of bleomycin-treated mice (FIGS. 12, 13). These results are totally consistent with those of Wang et al. (50) who used adenovirus rather than the CSD peptide to up-regulate caveolin-1 expression, thereby inhibiting the progression of bleomycin-induced lung fibrosis in mice. In addition to its effects on survival and tissue morphology, the CSD peptide blocked the changes in collagen, tenascin-C, ASMA, PKCε, and PKCα expression and the changes in the activation of ERK, JNK, and Akt that are normally associated with bleomycin-induced lung fibrosis (FIGS. 11, 13). Interestingly, CSD peptide treatment did not block the bleomycin-induced decrease in caveolin-1 expression (FIG. 11), strongly indicating that all the changes that were blocked are downstream from caveolin-1 in signaling cascades. In summary, the results strongly indicate that the low levels of caveolin-1 present in SLF and in the fibrotic lung tissue of SSc-ILD patients and bleomycin-treated mice lead to the activation of MEK, ERK, JNK, and Akt which in turn lead to the overexpression of collagen, tenascin-C, and ASMA.

Myofibroblasts are contractile, ASMA-positive fibroblasts that secrete high levels of ECM proteins and thus are key participants in the tissue remodeling that occurs during wound healing and in various fibrotic disorders (47,49). Originally, myofibroblasts were viewed as resident fibroblasts that became activated and proliferated due to their interaction with effector molecules present in fibrotic lung tissue, such as thrombin and TGFβ. In accord with this idea, thrombin and TGFβ induce the expression of collagen, tenascin-C, and ASMA by NLF (5,6,14). More recently, it has been proposed that myofibroblasts are generated by epithelial-mesenchymal transformation (18,52) and by the differentiation of bone marrow-derived stem cells into circulating, collagen-positive fibrocytes that traffic into injured lung tissue (21,25,26). Again, TGFβ and other pro-fibrotic cytokines promote epithelial-mesenchymal transformation (18,52), the differentiation of fibrocytes into myofibroblasts, and their expression of ECM proteins (2,15,26). Currently, it remains an open and controversial question as to whether all three potential sources contribute to the population of myofibroblasts present in fibrotic human lung tissue, or whether one source is predominant. In any case, low levels of caveolin-1 expression are a general feature of myofibroblasts regardless of whether they are derived from one source or from multiple sources. Therefore, treatments that increase the expression/function of caveolin-1 (e.g. CSD peptide) are beneficial in either scenario.

There have been relatively few studies on the signaling mechanisms controlling the myofibroblast phenotype (overexpression of ASMA and ECM proteins) in fibroblasts from normal and fibrotic lung tissue. The results are consistent with those in the most closely related previous study (50) in which it was found that using adenovirus to up-regulate caveolin-1 expression in cultured fibroblasts inhibited TGFβ-induced ECM protein expression by inhibiting the activation of JNK and ERK, and that adenovirus-mediated upregulation of caveolin-1 expression in vivo ameliorated bleomycin-induced lung fibrosis (50). The results are also consistent with the findings that JNK and PI3K/Akt signaling are involved in the regulation of ASMA expression (15,34,35). Other signaling molecules that are involved in the regulation of the myofibroblast phenotype and thus are likely to fit within the signaling pathways that are proposed herein (FIG. 14) include focal adhesion kinase, PTEN, and endothelin (20,34,35,40,51).

In summary, the study is a particularly comprehensive analysis of the signaling mechanisms underlying the regulation of the myofibroblast phenotype because fibroblasts were examined from both normal lung tissue and fibrotic lung tissue from SSc-ILD patients; the expression of ASMA, collagen, and tenascin-C were examined; signaling both in vitro and in vivo was examined; and several signaling molecules (caveolin-1, MEK, ERK, JNK, PI3K, Akt, PKCε, and PKCα) were examined. Of particular importance are the several pathways involving PI3K and Akt that were observed to function differently in NLF and SLF (FIG. 14).

The current studies have demonstrated that the CSD peptide can be used to up-regulate the function of caveolin-1 both in vitro and in vivo. These in vivo experiments provide proof of principle that the CSD peptide or a related agent can be used to treat lung fibrosis in human patients. While experiments using adenovirus are an elegant way to demonstrate the ability of caveolin-1 to ameliorate the progression of lung fibrosis in an animal model (50), a pharmacological agent such as the CSD peptide that mimics the function of caveolin-1 is more likely than adenovirus infection to gain approval for use in human patients. Of course, there is still considerable room for improvement in the CSD peptide. The version used in the current study contains 16 amino acids from the Antennapedia internalization sequence to mediate its entry into cells and 20 amino acids from the caveolin-1 scaffolding domain.

2. Example 2

The CSD Peptide and its Subdomains Differ in their Ability to Inhibit Collagen and ASMA Expression and in their Effects on NLF and SLF Herein "improved" versions of the CSD peptide better able to inhibit the expression of collagen by lung fibroblasts in vitro and inhibit the progression of bleomycin-induced lung fibrosis in vivo are identified. One set of candidates for improved versions of the CSD peptide is subdomains of the caveolin-1 scaffolding domain. Indeed, these subdomains have already successfully used in vitro.

To compare the activity of CSD to its subdomains, five subdomains [A (82-88 amino acids), B (89-95), C (96-101), AB (82-95) and BC (89-101)] were synthesized in fusion with the Antennapedia internalization sequence and added to culture medium at 1, 3, and 5 μM. Subdomains A and B did not inhibit collagen or ASMA expression at any concentration tested. Intact CSD and BC completely inhibited collagen expression in both NLF and SLF at 3 μM (FIG. 15). C and AB were also effective in both cell types at inhibiting collagen expression, but were somewhat less active in that they provided approximately 50% inhibition at 5 μM. Very different results were obtained when examining ASMA expression. Intact CSD and C inhibited ASMA expression in SLF, but not in NLF. BC inhibited ASMA expression in both cell types whereas AB did not inhibit ASMA expression in either cell type. Intact CSD (in SLF) and BC (in both cell types) were the most effective, inhibiting ASMA expression by about 80% at 5 μM. C was somewhat less effective, inhibiting ASMA expression by about 50% at 5 μM (in SLF). In addition to the differences between the effect of each peptide on the expression of collagen and ASMA and the differences between NLF and SLF in their response to a given peptide, the results were also very different than those of Bernatchez et al. (4) who examined the sensitivity of eNOS activity in endothelial cells to these same peptides. eNOS activity was most strongly inhibited by intact CSD and B and was also inhibited by AB and BC. The results and those of Bernatchez et al. (4) are summarized in Table 2 and demonstrate that the ability of each peptide to regulate the expression of a particular target protein depends on the target protein and on the cell type.

TABLE 2

Ability of CSD and its subdomains to inhibit collagen, ASMA, and eNOS expression

| Peptide | Collagen | | ASMA | | eNOS |
|---|---|---|---|---|---|
| | NLF | SLF | NLF | SLF | End |
| CSD | ++ | ++ | − | ++ | + |
| A | − | − | − | − | − |
| B | − | − | − | − | + |
| C | + | + | − | + | − |
| AB | + | + | − | − | + |
| BC | ++ | ++ | ++ | ++ | + |

Collagen and ASMA data are from FIG. 11, eNOS is from (38). End, endothelial cells.

3. Example 3

CBD Families

Although a consensus sequence (ΦXΦXXXXΦXXΦ where Φ stands for any of the aromatic amino acids (F, W, or Y) and X stands for any amino acid) present in many proteins that bind to caveolin-1 was identified years ago through the use of a phage-display library (57), little progress has been made since in characterizing these caveolin-1-binding domains (CBDs). Because PKC isoforms, MAP kinases, and PI3 Kinases (FIG. 14) were identified as critical intermediates in the regulation of collagen expression by the CSD peptide, the CBDs present in these classes of molecules were examined identifying novel peptides that specifically interfere with the interaction between caveolin-1 and a very limited number of its binding partners. Remarkably, several families of CBD sequences are present in these kinase families that are present, with one exception, in almost no other proteins in the human genome. That exception, family 7, has members among the PKCs, the MAP Kinases, the Tec family (involved in Akt-independent PI3K signaling), several well-known receptor tyrosine kinases, and several well-known non-receptor tyrosine kinases. However, family 7 can be pared down into three subfamilies (7a, 7b, 7c) that are essentially specific for PKCs, MAP Kinases, and Tec family members respectively. Another noteworthy observation is that the aromatic amino acids can be dispensable in defining a family. For example, although the sequence SCAG is present at positions 4-7 in all ten PI3 Kinases in family 12, many of these family members do not have aromatic amino acids at positions 3 and 8 and none of the family members have an aromatic amino acid at position 11. It is also noteworthy that some of these kinases fall into more than one family. For example, PKCα contains CBDs from families 1, 2, and 7a and PKCε contains CBDs from families 6 and 7a.

TABLE 3

CBD Families in PKC Isoforms, MAP Kinases, and PI3K Signaling

Family Sequences (11-amino acid sequences, N-terminal to C-terminal)

| Family # | 1 | 2 | 3 | 4 | 5 | 6 |
|---|---|---|---|---|---|---|
| 1 | W | G | F | G | K | Q |
| 2 | F | ST | FY | VT | N | P |
| 3 | F | M | Y | P | PA | NS |
| 4 | Y | GT | F | S | V | D |
| 5 | HY | SN | Y | K | AS | P |
| 6 | H | P | YF | L | VT | NQ |
| 7 | FW | ASG | FWYML | G | LIV | LIVT |
| 7a | W | AS | FYML | G | V | L |
| 7b | FW | S | FWY | G | VI | LIV |
| 7c | W | AS | F | G | VI | L |
| 8 | SC | SP | Y | I | VI | GQ |
| 9 | Y | A | W | A | P | K |
| 10 | Y | D | Y | R | S | S |
| 11 | AKY | PHR | YFW | PLY | R | KIS |
| 12 | FY | IVFT | YRLKQ | S | C | A |
| 13 | FRY | L | W | EFS | KYH | R |

Family Sequences (11-amino acid sequences, N-terminal to C-terminal)

| Family # | 7 | 8 | 9 | 10 | 11 |
|---|---|---|---|---|---|
| 1 | G | F | Q | C | Q |
| 2 | QEKD | F | VE | HI | PNL |
| 3 | P | W | KSR | EH | I |
| 4 | W | W | AS | FL | G |
| 5 | T | F | C | DE | HY |
| 6 | L | FY | CAG | C | F |
| 7 | LVM | WYHTM | E | LIVTAM | FYLITVM |
| 7a | LM | YF | E | M | LM |
| 7b | L | W | E | LV | LI |
| 7c | M | W | E | VI | FY |
| 8 | FC | YF | G | AT | F |
| 9 | P | Y | H | K | F |
| 10 | IL | W | S | CL | G |
| 11 | A | FY | NDP | S | EY |
| 12 | G | CWY | C | VL | AVI |
| 13 | YFH | Y | C | FHNV | KSNT |

PKCs

| | |
|---|---|
| PKCalpha | 1 |
| PKCbeta | 1 |
| PKCalpha | 2 |
| PKCbeta | 2 |
| PKCgamma | 2 |
| PKCdelta | 2 |
| PKCmu | 3 |
| nPKC-D2 | 3 |
| PKCnu | 3 |
| PKCdelta | 4 |
| PKCiota | 4 |
| PKCzeta | 4 |
| PKCnu | 5 |
| PKCtheta | 5 |
| PKCepsilon | 6 |
| PKCeta | 6 |
| PKC-like 1 | 6 |
| PKC-like 2 | 6 |
| PKCalpha | 7a |
| PKCbeta | 7a |
| PKCgamma | 7a |
| PKCdelta | 7a |
| PKCeta | 7a |
| PKCtheta | 7a |
| PKCepsilon | 7a |
| PKCiota | 7a |
| PKCzeta | 7a |
| PKCdelta | 11 |

TABLE 3-continued

CBD Families in PKC Isoforms, MAP Kinases, and PI3K Signaling

MAP Kinases

| | |
|---|---|
| M3K7 | 7b |
| M3K9 | 7b |
| M3K10 | 7b |
| M3K11 | 7b |
| M3K12 | 7b |
| M3K13 | 7b |
| M3KL4 | 7b |
| MP2K1 (MEK1) | 8 |
| MP2K2 (MEK2) | 8 |
| MP2K5 | 8 |
| MP2K7 | 8 |
| M4K4 | 9 |
| MINK1 | 9 |
| M4K4 | 10 |
| MINK1 | 10 |
| M3K6 | 11 |
| M3K8 | 11 |

PI3 Kinases

| | |
|---|---|
| PI3K p110alpha | 12 |
| PI3K p110beta | 12 |
| PI3K p110gamma | 12 |
| PI3K p110delta | 12 |
| PI3K C2alpha | 12 |
| PI3K C2beta | 12 |
| PI3K C2gamma | 12 |
| PI3K C2delta | 12 |
| PI4Kbeta | 12 |
| PI3K type 3 | 12 |
| PI3K C2alpha | 13 |
| PI3K C2beta | 13 |
| PI3K C2gamma | 13 |
| P3K p110alpha | 13 |

Tec family (involved in Akt-independent PI3K signaling)

| | |
|---|---|
| BMX | 7c |
| BTK | 7c |
| ITK | 7c |
| TEC | 7c |
| TXK | 7c |

Family 7 Receptor Tyr Kinases (partial list)

| | |
|---|---|
| DDR1 | Flt3 |
| DDR2 | PDGFRalpha |
| EphA1 | PDGFRbeta |
| EphA8 | VEGFR1 |
| FGFR1 | VEGFR2 |
| FGFR2 | VEGFR3 |
| FGFR3 | Tie1 |
| FGFR4 | Tie2 |

Family 7 Non-Receptor Tyr Kinases (partial list)

Csk
Fer
Fes
Frk
Fyn
Jak1
Jak2
Jak3
Lck
Lyn
Src

4. Example

Improved Versions of the CSD Peptide

Three independent approaches can be taken to improve the CSD peptide. To accomplish this, a determination is first made as to whether subdomains of the CSD peptide are as active, or perhaps more active, than the intact peptide. Experiments with these subdomains on lung fibroblasts in vitro are essentially complete and were highly successful (see FIG. 15 and Table 2). In particular, the BC peptide was as effective as the full-length CSD peptide in inhibiting collagen and ASMA expression while the AB and C peptides had partial activity. In one aspect, for example, these shorter peptides can be more active in vivo than the full-length CSD peptide because they are more soluble and thus better able to reach target tissues and because they are of greater purity due to their shorter length.

In the second approach, myristoylation is used rather than the Antennapedia internalization sequence to carry peptides across the plasma membrane. This approach is very promising because it has already been used to carry the CSD peptide into cells, resulting in the inhibition of endothelin-induced ERK activation in mesangial cells (29). This approach results in the use of peptides that are much shorter and therefore much less costly, that are of greater purity due to their shorter length, and that are better able to enter cells in vitro and to reach target tissues when used in vivo. Myristoylated peptides are likely to remain associated with membranes, rather than enter the cytoplasm or nucleus. Therefore, myristoylated peptides have more of an effect on signaling than peptides containing the Antennapedia internalization sequence because signaling cascades are usually associated with cellular membranes. Finally, both the first and second approaches can be combined. Namely, functional subdomains of the CSD peptide are synthesized with myristoyl groups, rather than the Antennapedia internalization sequence, to carry them across membranes.

Peptoids are oligo(N-alkyl) glycines that differ from peptides in that side chains are connected to the amide nitrogens rather than to the lx carbon atoms. In the third approach, a peptoid is synthesized with side chains equivalent to those in the CSD peptide. This CSD peptide-like peptoid (CSD peptoid) has the function of the CSD peptide, yet it also has the resistance to proteolysis or enzymatic modification of a peptidomimetic drug. Therefore, this CSD peptoid is suitable for use in human patients. The CSD peptoid is attached to a standard peptide Antennapedia internalization sequence. This CSD peptoid can be improved by: 1) using peptoid internalization sequences that are reported to be much more effective than the Antennapedia peptide (59), 2) making a myristoylated CSD peptoid, 3) making peptoids with side chains equivalent to the subdomains of the CSD peptide that are found to be active in the first approach, and 4) making myristoylated peptoids with side chains equivalent to active subdomains of the CSD peptide.

G. References

1. Anderson R G. The caveolae membrane system. *Annu Rev Biochem*, 67:199-225, 1998.
2. Bellini A, Mattoli S. The role of the fibrocytes, a bone marrow-derived mesenchymal progenitor, in reactive and reparative fibrosis. *Lab Invest,* 2007, (In Press).
3. Beon M, Harley R A, Wessels A, Silver R M, Ludwicka-Bradley A. Myofibroblast induction and microvascular alteration in scleroderma lung fibrosis. *Clin Exp Rheumatol,* 22: 733-742, 2004.
4. Bernatchez P, Bauer P, Yu J, Prendergast J, He P, Sessa W. Dissecting the molecular control of endothelial NO synthase by caveolin-1 using cell-permeable peptides. *Proc Natl Acad Sci USA,* 102:761-766, 2005.
5. Bogatkevich G S, Tourkina E, Silver R M, Ludwicka-Bradley A. Thrombin differentiates normal lung fibroblasts to a myofibroblast phenotype via the proteolytically activated receptor-1 and a protein kinase C-dependent pathway. *J Biol Chem*, 276:45184-45192, 2001.
6. Bogatkevich G, Tourkina E, Abrams C S, Harley R A, Silver R M, Ludwicka-Bradley A. Contractile activity and smooth muscle-ax actin organization in thrombin-induced human lung myofibroblasts. *Am J Physiol Lung Cell Mol Physiol,* 85:L334-L343, 2003.
7. Bucci M, Gratton J-P, Rudic R D, Acevedo L, Roviezzo F, Cirino G, Sessa W C. In vivo delivery of the caveolin-1 scaffolding domain inhibits nitric oxide synthesys and reduces inflammation. *Nature Med,* 6:1362-1367, 2000.
8. Cohen A W, Park D S, Woodman S E, Williams T M, Chandra M, Shirani J, Pereira de Souza A, Kitsis R N, Russell R G, Weiss L M. Caveolin-1 null mice develop cardiac hypertrophy with hyperactivation of p42/44 MAP kinase in cardiac fibroblasts. *Am J Physiol Cell Physiol* 284:C457-474, 2003.
9. Couet J, Sargiacomo M, and Lisanti, M P. Interaction of a receptor tyrosine kinase, EGFR, with caveolins. Caveolin binding negatively regulates tyrosine and serine/threonine kinase activities. *J Biol Chem* 272:30429-30438, 1997.
10. Cui J, Holgado-Magruda M, Su W, Tsuiki H, Wedegaertner P, Wong A J. Identification of specific domain responsible for JNK2α2 autophosphorylation. *J Biol Chem,* 280: 9913-9920, 2005.
11. Drab M, Vercade P, Elger M, Kasper M, Lohn M, Lauterbach B., Menne J., Lindschau C., Mende F., Luft F. C., Schedl A., Haller H., and Kurzchalia T. V. Loss of caveolae, vascular dysfunction, and pulmonary defects in caveolin-1 gene-disrupted mice. *Science,* 293:2449-2452, 2001.
12. Finch W R, Rodnan G P, Buckingham R B, Prince R K, Winkelstein A. Bleomycin-induced scleroderma. *J Rheumatol,* 7:651-659, 1980.
13. Galbiati F, Volonte D, Gil O, Zanazzi G, Salzer J, Sargiacomo M, Scherer P E, Engelman J A, Schlegel A, Parenti M. Expression of caveolin-1 and -2 in differentiating PC12 cells and dorsal root ganglion neurons: caveolin-2 is up-regulated in response to cell injury. *Proc Natl Acad Sci USA,* 95:10257-10262, 1998.
14. Gray A J, Bishop J E, Reeves J T, Mecham R P, Laurent G J. Partially degraded fibrin(ogen) stimulates fibroblast proliferation in vitro. *Am J Respirator Cell Mol Biol,* 12: 684-690, 1995.
15. Hong K M, Belperio J B, Keane M P, Burdick M D, Strieter R M. Differentiation of human circulating fibrocytes as mediated by transforming growth factor-beta and peroxisome proliferators activated receptor-gamma *J Biol Chem,* 2007 (In Press).
16. Hua H, Munk S, Whiteside C I. Endothelin-1 activates mesangial cell ERK1/2 via EGF-receptor transactivation and caveolin-1 interaction. *Am J Physiol Renal Physiol,* 284:F303-312, 2003.
17. Kasper M, Reimann T, Hempe, U, Wenze K W, Bierhaus A, Schuh D, Dimmer V, Haroske G, Muller M. Loss of caveolin-1 expression in type I pneumocytes as an indicator of subcellular alterations during lung fibrogenesis. *Histochem Cell Biol,* 109:41-48, 1998.
18. Kim K K, Kudler M C, Wolters P J, Robillard L, Galvez M G, Brumwell A N, Sheppard D, Chapman N A. Alveolar epithelial cell mesenchymal transition develops in vivo during pulmonary fibrosis and is regulated by the extracellular matrix. *Proc Natl Acad Sci USA,* 103: 13180-13185, 2006.
19. Lisanti M, Scherer P, Vidugiriene J, Tang Z, Hermanowski-Vosatka A, Tu Y-H, Cook R, Sargiacomo M. Characterization of caveolin-rich membrane domains isolated from an endothelial-rich source: implications for human disease. *J Biol Chem,* 126: 111-126, 1994.

20. Mimura Y, Ihn H, Jinnin M, Asano Y, Yamane K, Tamaki K. Constitutive phosphorylation of focal adhesion kinase is involved in the myofibroblast differentiation of scleroderma fibroblasts. *J Invest Dermatol,* 124: 886-892, 2005.
21. Moore B B, Kolodsick J E, Thanninckal V J, Cooke K, Moore T A, Hogaboam C, Wilke C A, Toews G B. CCR2-mediated recruitment of fibrocytes to the alveolar space after fibrotic injury. *Am J Pathol,* 166: 675-684, 2005.
22. Oka N, Yamamoto M, Schwencke C, Kawabe J-I, Ebina T, Ohno S, Couet J, Lisanti M P, Ishikawa Y. Caveolin interaction with protein kinase C. *J Biol Chem,* 272:33416-33421, 1997.
23. Okamoto T, Schlegel A, Scherer P E, Lisanti M P. Caveolins, a family of scaffolding proteins for organizing 'preassembled signaling complexes' at the plasma membrane. *J Biol Chem,* 273:5419-5422, 1998.
24. Pannu J, Nakerakanti S, Smith E, Dijke P, and Trojanowska M. Transforming Growth Factor-β receptor type I-dependent fibrogenic gene programs mediated via activation of Smad1 and ERK1/2 pathways. *J Biol Chem,* 282; 10405-10413, 2007.
25. Phillips R J, Burdick M D, Hong K, Lutz M A, Murray L A, Xue Y Y, Belperio J A, Keane M P, Strieter R M. Circulating fibrocytes traffic to the lungs in response to CXCL12 and mediate fibrosis. *J Clin Invest,* 114: 438-446, 2004.
26. Quan T E, Cowper S E, Bucala R. The role of the circulating fibrocytes in fibrosis. *Curr Rheumatol Rep,* 8: 145-150, 2006.
27. Razani B, Rubin C S, Lisanti M P. Regulation of cAMP-mediated signal transduction via interaction of caveolins with the catalytic subunit of protein kinase A. *J Biol Chem,* 274:26353-26360, 1999.
28. Razani B, Engelman J A, Wang X B, Schubert W, Zhang X L, Marks C B, Macaluso F, Russel, R G, Li M, Pestell R G, Di Vizio D, Hou H Jr, Kneitz B, Lagaud G, Christ G J, Edelmann W, Lisanti M P. Caveolin-1 null mice are viable but show evidence of hyperproliferative and vascular abnormalities. *J Biol Chem,* 276:38121-38138, 2001.
29. Razani B, Woodman S, Lisanti M. Caveolae: from cell biology to animal physiology. *Pharmacol Rev,* 54:431-467, 2002.
30. Rybin V O, Xu X, Steinberg S F. Activated protein kinase C isoforms target to cardiomyocyte caviolae: stimulation of local protein phosphorylation. *Circ Res,* 84: 980-988, 1999.
31. Scherer P E, Tang Z., Chun M, Sargiacomo M, Lodish H F, Lisanti M P. Caveolin isoforms differ in their N-terminal protein sequence and subcellular distribution. Identification and epitope mapping of an isoform-specific monoclonal antibody probe. *J Biol Chem,* 270:16395-16401, 1995.
32. Sedding D G, Hermsen J, Seay U, Eickelberg O, Kummer W. Schwencke C, Strasser R H, Tillmanns H, and Braun-Dullaeus R C. Caveolin-1 facilitates mechanosensitive protein kinase B (Akt) signaling in vitro and in vivo. *Circ Res* 96; 635-642, 2005.
33. Shaul P and Anderson R. Role of plasmalemmal caveolae in signal transduction. *AJP Lung Cell Mol Phys,* 275:L843-L851, 1998.
34. Shi-wen X, Chen Y, Denton C P, Eastwood M, Renzoni E A, Bou-Gharios G, Pearson J D, Dashwood M, duBois R M, Black C M, Leask A, Abraham D J. Endothelin-1 promotes myofibroblast induction through the ETA receptor via a rac/PI3 kinase/Akt-dependent pathway and is essential for the enhanced contractile phenotype of fibrotic fibroblasts. *MBC,* 15: 2707-2719, 2004.
35. Shi-Wen X, Rodríguez-Pascual F, Lamas S, Holmes A, Howat S, Pearson J P, Dashwood M R, du Bois R M, Denton C P, Black C M, Abraham D J, and Leask A. Constitutive ALK5-independent c-Jun N-Terminal Kinase activation contributes to endothelin-1 overexpression in pulmonary fibrosis: evidence of an autocrine endothelin loop operating through the endothelin A and B receptors. *Mol Cel Biol,* 26; 5518-5527, 2006.
36. Song K S, Li S, Okamoto T, Guilliam L A, Sargiacomo M, Lisanti M P. Co-precipitation and direct interaction of Ras with caveolin, an integral membrane protein of caveolae microdomains. *J Biol Chem,* 271:9690-9697, 1996.
37. Sowa G, Pypaert M, Sessa W. Distinction between signaling mechanisms in lipid rafts vs. caveolae. *Proc Natl Acad Sci USA,* 98: 14072-14077, 2001.
38. Steen V D, Medsger T A. Changes in causes of death in systemic sclerosis. *Ann Rheum Dis,* 66: 940-944, 2007.
39. Tashkin D P, Elashoff R, Clements P J, Goldin J, Roth M D, Furst D E, Arriola E, Silver R, Strange C. Bolster M, Seibold J R, Riley D J, Hsu V M, Varge J, Schaufnagel D E, Theodore A, Simms R, Wise R, Wigley F, White B, Steen V, Read C, Mayes M, Parsley E, Mubarak K, Connoly M K, Golden J, Olman M, Fessler B, Rothfield N, Metersky M. Scleroderma Lung Study Research Group. Cyclophosphamide versus placebo in scleroderma lung disease. *N Engl J Med,* 354: 2655-2666, 2006.
40. Thannickal V J, Lee D Y, White E S, Cui Z, Larios J M, Chacon R, Horowitz J C, Day R M, Thomas P E. Myofibroblast differentiation by transforming growth factor-beta 1 is dependent on cell adhesion and integrin signaling via focal adhesion kinase. *J Biol Chem,* 278: 12384-12389, 2003.
41. Toker A, and Newton A. Akt/Protein Kinase B regulated by autophosphorylation in the hypothetical PDK-2 site. *J Biol Chem,* 275: 8271-8274, 2000.
42. Tourkina E, Hoffman S, Fenton J W II, Silver R M, Ludwicka-Bradley A. Depletion of PKC-epsilon in normal and scleroderma lung fibroblasts has opposite effects on tenascin expression. *Arthritis and Rheum,* 44:1370-1381, 2001.
43. Tourkina E, Gooz P, Oates J C, Ludwicka-Bradley A, Silver R M, Hoffman S. Curcumin-induced apoptosis in scleroderma lung fibroblasts: Role of protein kinase Ce. *American Journal of Respiratory Cellular and Molecular Biology,* 31:28-35, 2004.
44. Tourkina E, Gooz P, Pannu, J, Bonner M, Scholz D, Hacker S, Silver R M, Trojanowska M, and Hoffman S. Opposing effects of protein kinase C alpha and protein kinase C epsilon on collagen expression by human lung fibroblasts are mediated via MEK/ERK and caveolin-1 signaling. *J Biol Chem,* 280:13879-13887, 2005.
45. Tourkina E, Richard M, Charles K, Silver R M, Hoffman S. Caveolin-1 regulates collagen expression through MEK/ERK signaling and differentiation normal lung fibroblasts in myofibroblasts. ASCB Meeting, Washington, D.C., December 2005, Abstract.
46. Tourkina E, Richard M, Bonner M, Silver R M, Hoffman S. Anti-fibrotic and anti-inflammatory roles of caveolin-1 in scleroderma. ASCB Meeting, San-Diego, December 2006,
47. Uhal B, Joshi I, Hughes W F, Ramos C, Pardo A, Selman M. Alveolar epithelial cell death adjacent to underlying myofibroblasts in advanced fibrotic human lung. *Am J Physiol Lung Cell Mol Physiol* 1998; 275:L1192-L1199.
48. Van de Water J, Jiminez S A, Gershwin M E. Animal models of scleroderma: contrasts and comparisons. *Intern Rev Immunol* 1995; 12:201-216.

49. Vyalov S L, Gabbiani G, and Kapanci Y. Rat alveolar myofibroblasts acquire alpha-smooth muscle actin expression during bleomycin-induced pulmonary fibrosis. *Am J Pathol* 1993; 143: 1754-1765.
50. Wang X M, Zhang Y, Kim H P, Zhou Z, Feghali-Bostwick C A, Liu F, Ifedigbo E, Xu X, Oury T D, Kaminski N, and Choi A M K. Caveolin-1: a critical regulator of lung fibrosis in idiopathic pulmonary fibrosis. *J Exp Med*, 203; 2895-2906, 2006.
51. White ES, Atrasz R G, Hu B, Phan S H, Stambolic V, Mac T W, Hogaboam C M, Flaherty K R, Martinez F J, Kontos C D, Toews G B. Negative regulation of myofibroblast differentiation by PTEN (Phosphatase and Tensin Homolog deleted on chromosome 10). *Am J Respir Crit. Care Med*, 173: 112-121.
52. Wu Z, Yang L, Cai L, Zhang M, Cheng X, Yang X, Xu J. Detection of epithelial to mesenchymal transition in airways of a bleomycin induced pulmonary fibrosis model derived from an alpha-smooth muscle actin-Cre transgenic mouse. *Respir Res*, 8: 1, 2007.
53. Yamamoto T, Takagawa S, Katayama I, Yamazaki Y, Shinkai H, Nashioka K. Animal model of sclerotic skin I: local injections of bleomycin induce sclerotic skin mimicking scleroderma. *J Invest Dermatol*, 112:456-462, 1999.
54. Zhang H, Gharaee-Kermani M, Zhang K, Karmiol S, Phan S H. Lung fibrosis, alpha-smooth muscle actin expression and contractile phenotype in bleomycin-induced pulmonary fibrosis. *Am J Pathol*, 148:527-537, 1996.
55. Silver, R. M. 1995. Interstitial lung disease of systemic sclerosis. *Int Rev Immunol* 12:281-291.
56. Altman, R. D., Medsger, T. A., Jr., Bloch, D. A., and Michel, B. A. 1991. Predictors of survival in systemic sclerosis (scleroderma). Arthritis Rheum 34:403-413.
57. Couet, J., Li, S., Okamoto, T., Ikezu, T., and Lisanti, M. P. 1997. Identification of peptide and protein ligands for the caveolin-scaffolding domain. Implications for the interaction of caveolin with caveolae-associated proteins. *J Biol Chem* 272:6525-6533.
58. Muller, G., Jung, C., Wied, S., Welte, S., Jordan, H., and Frick, W. 2001. Redistribution of glycolipid raft domain components induces insulin-mimetic signaling in rat adipocytes. *Mol Cell Biol* 21:4553-4567.
59. Wender, P. A., Mitchell, D. J., Pattabiraman, K., Pelkey, E. T., Steinman, L., and Rothbard, J. B. 2000. The design, synthesis, and evaluation of molecules that enable or enhance cellular uptake: peptoid molecular transporters. *Proc Natl Acad Sci USA* 97:13003-13008.

---

What is claimed is:

1. A method of treating fibrosis in a subject in need thereof comprising administering to the subject a composition comprising a caveolin-1 scaffolding domain (CSD) moiety as set forth in SEQ ID NO: 1 or a fragment thereof comprising the B and C subdomains of CSD.

2. The method of claim 1, wherein the CSD moiety is a peptide.

3. The method of claim 2, wherein the peptide is a fusion peptide comprising the caveolin-1 scaffolding domain and the C-terminus of an Antennapedia internalization sequence.

4. The method of claim 3, wherein the C-terminus of the Antennapedia internalization sequence is set forth as in SEQ ID NO: 3.

5. The method of claim 2, wherein the peptide has been myristoylated.

6. The method of claim 2, wherein the peptide has been modified to be a peptoid.

7. The method of claim 1, wherein the CSD moiety is a peptidomimetic.

8. The method of claim 1, further comprising administering to the subject curcumin.

9. The method of claim 1, wherein the fibrosis is pulmonary fibrosis caused by scleroderma lung disease, idiopathic pulmonary fibrosis (IPF), Bronchiolitis Olibterans Organizing Pneumonia (BOOP), Acute Respiratory Distress Syndrome (ARDS), asbestosis, accidental radiation induced lung fibrosis, therapeutic radiation induced lung fibrosis, Rheumatoid Arthritis, Sarcoidosis, Silicosis, Tuberculosis, Hermansky Pudlak Syndrome, Bagassosis, Systemic Lupus Erythematosis, Eosinophilic granuloma, Wegener's granulomatosis, Lymphangioleiomyomatosis, Cystic Fibrosis, Nitiofurantoin exposure, Amiodarone exposure, Bleomycin exposure, cyclophosphamide exposure, or methotrexate exposure.

10. The method of claim 1, wherein the fibrosis results from myocardial infarction, injury related tissue scarring, scarring form surgery, or therapeutic radiation induced fibrosis.

* * * * *